United States Patent
Lim et al.

(10) Patent No.: US 9,627,624 B2
(45) Date of Patent: Apr. 18, 2017

(54) COMPOUND FOR ORGANIC OPTOELECTRONIC DEVICE ORGANIC LIGHT EMITTING DIODE INCLUDING THE SAME AND DISPLAY INCLUDING THE ORGANIC LIGHT EMITTING DIODE

(71) Applicant: SAMSUNG DISPLAY CO., LTD., Yongin, Gyeonggi-Do (KR)

(72) Inventors: Jin-O Lim, Yongin (KR); Seok-Hwan Hwang, Yongin (KR); Young-Kook Kim, Yongin (KR); Hye-Jin Jung, Yongin (KR); Jun-Ha Park, Yongin (KR); Eun-Young Lee, Yongin (KR); Sang-Hyun Han, Yongin (KR); Eun-Jae Jeong, Yongin (KR); Soo-Youn Kim, Yongin (KR); Jong-Hyuk Lee, Yongin (KR)

(73) Assignee: Samsung Display Co., Ltd., Yongin, Gyunggi-do (KR)

( * ) Notice: Subject to any disclaimer, the term of this patent is extended or adjusted under 35 U.S.C. 154(b) by 352 days.

(21) Appl. No.: 14/269,281

(22) Filed: May 5, 2014

(65) Prior Publication Data
US 2015/0014656 A1    Jan. 15, 2015

(30) Foreign Application Priority Data

Jul. 12, 2013 (KR) .................. 10-2013-0082256

(51) Int. Cl.
*H01L 51/00*    (2006.01)
*C07D 409/14*    (2006.01)
(Continued)

(52) U.S. Cl.
CPC ........ *H01L 51/0058* (2013.01); *C07B 59/002* (2013.01); *C07D 209/86* (2013.01);
(Continued)

(58) Field of Classification Search
None
See application file for complete search history.

(56) References Cited

U.S. PATENT DOCUMENTS

| 5,972,247 A | 10/1999 | Shi et al. |
| 6,465,115 B2 | 10/2002 | Shi et al. |
| (Continued) | | |

FOREIGN PATENT DOCUMENTS

| JP | 08-012600 A | 1/1996 |
| JP | 11-144866 A | 5/1999 |
| (Continued) | | |

*Primary Examiner* — J. L. Yang
(74) *Attorney, Agent, or Firm* — Lee & Morse, P.C.

(57) ABSTRACT

A compound for an organic optoelectronic device is represented by the following Chemical Formula 1.

[Chemical Formula 1]

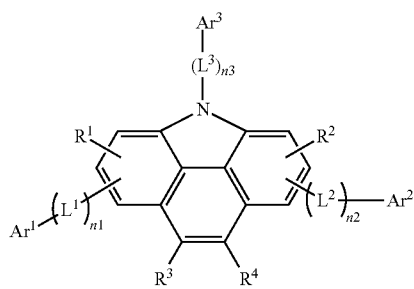

wherein $R^1$, $R^2$, $R^3$, $R^4$, $Ar^1$, $Ar^2$, $Ar^3$, $L^1$, $L^2$, $L^3$, $n^1$, $n^2$, and $n^3$ are further defined in the specification.

15 Claims, 3 Drawing Sheets

(51) Int. Cl.
*C07D 405/14* (2006.01)
*C07D 209/86* (2006.01)
*C07F 7/08* (2006.01)
*C07B 59/00* (2006.01)
*H01L 51/50* (2006.01)

(52) U.S. Cl.
CPC ......... *C07D 405/14* (2013.01); *C07D 409/14* (2013.01); *C07F 7/0814* (2013.01); *H01L 51/0052* (2013.01); *H01L 51/0054* (2013.01); *H01L 51/0072* (2013.01); *H01L 51/0094* (2013.01); *H01L 51/0081* (2013.01); *H01L 51/5012* (2013.01)

(56) References Cited

U.S. PATENT DOCUMENTS

| | | |
|---|---|---|
| 6,596,415 B2 | 7/2003 | Shi et al. |
| 2014/0110676 A1* | 4/2014 | Kim .................... C07D 403/04 257/40 |

FOREIGN PATENT DOCUMENTS

| | | |
|---|---|---|
| JP | 2000-003782 A | 1/2000 |
| JP | 2005-048004 A | 2/2005 |
| JP | 2009-215333 A | 9/2009 |
| KR | 10-2009-0128382 A | 12/2009 |

\* cited by examiner

COMPOUND FOR ORGANIC OPTOELECTRONIC DEVICE ORGANIC LIGHT EMITTING DIODE INCLUDING THE SAME AND DISPLAY INCLUDING THE ORGANIC LIGHT EMITTING DIODE

CROSS-REFERENCE TO RELATED APPLICATION

Korean Patent Application No. 10-2013-0082256, filed on Jul. 12, 2013, in the Korean Intellectual Property Office, and entitled: "Compound For Organic Optoelectronic Device, Organic Light Emitting Diode Including The Same and Display Including The Organic Light Emitting Diode," is incorporated by reference herein in its entirety.

BACKGROUND

1. Field

Embodiments relate to an organic optoelectronic device, an organic light emitting diode including the same, and a display device including the organic light emitting diode.

2. Description of the Related Art

An organic photoelectric device is a device requiring a charge exchange between an electrode and an organic material by using holes or electrons.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows. A voltage or a current is applied to at least two electrodes to inject holes and/or electrons into an organic material semiconductor positioned at interfaces of the electrodes, and the device is driven by the injected electrons and holes.

SUMMARY

Embodiments are directed to a compound for an organic optoelectronic device, the compound being represented by the following Chemical Formula 1:

[Chemical Formula 1]

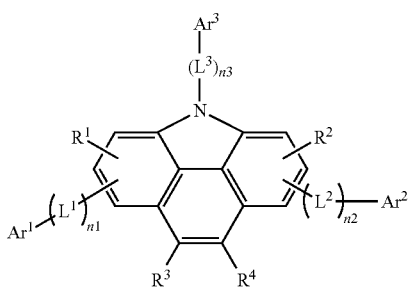

wherein, in the above Chemical Formula 1, $Ar^1$ and $Ar^2$ are each independently a substituted or unsubstituted C6 to C30 aryl group, or a substituted or unsubstituted C2 to C30 heteroaryl group, $R^1$ to $R^4$ and $Ar^3$ are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group, $L^1$ to $L^3$ are each independently a substituted or unsubstituted C6 to C30 arylene group or a substituted or unsubstituted C2 to C30 heteroarylene group, and n1 to n3 are each independently integers of 0 to 3.

The compound for an organic optoelectronic device may be represented by the following Chemical Formula 2:

[Chemical Formula 2]

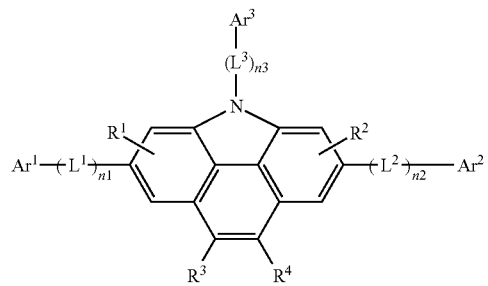

wherein in the above Chemical Formula 2, $Ar^1$ and $Ar^2$ are each independently a substituted or unsubstituted C6 to C30 aryl group, or a substituted or unsubstituted C2 to C30 heteroaryl group, $R^1$ to $R^4$ and $Ar^3$ are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group, $L^1$ to $L^3$ are each independently a substituted or unsubstituted C6 to C30 arylene group or a substituted or unsubstituted C2 to C30 heteroarylene group, and n1 to n3 are each independently integers of 0 to 3.

$Ar^1$ and $Ar^2$ may each independently be a substituted or unsubstituted C6 to C30 aryl group.

$Ar^1$ and $Ar^2$ may each be independently a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group.

At least one of $Ar^1$ and $Ar^2$ may be a substituted or unsubstituted dibenzofuranyl group, a substituted or unsubstituted dibenzothiophenyl group, a substituted or unsubstituted carbazolyl group, or a substituted or unsubstituted fluorenyl group.

$L^1$ to $L^3$ may each independently be a substituted or unsubstituted phenylene group, or a substituted or unsubstituted naphthalene group.

$Ar^3$ may be a substituted or unsubstituted phenyl group, or a substituted or unsubstituted biphenyl group.

At least one of $Ar^1$ and $Ar^2$ may be a silyl group, a cyano group, deuterium, a halogen, or a C6 to C30 aryl group substituted with a C1 to 10 alkyl group.

Embodiments are also directed to an organic light emitting diode including an anode, a cathode, and at least one organic thin layer interposed between the anode and cathode. At least one organic thin layer includes the compound for an organic optoelectronic device.

The organic thin layer may include an electron injection layer (EIL), an electron transport layer (ETL), a hole injection layer (HIL), a hole transport layer (HTL), or an emission layer.

The organic thin layer may be an electron injection layer (EIL), or an electron transport layer (ETL).

The organic thin layer may be an emission layer.

The compound may be used as a host in an emission layer.

The compound may be used as a red, green, blue, or white host in an emission layer.

A display device may include the organic light emitting diode.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
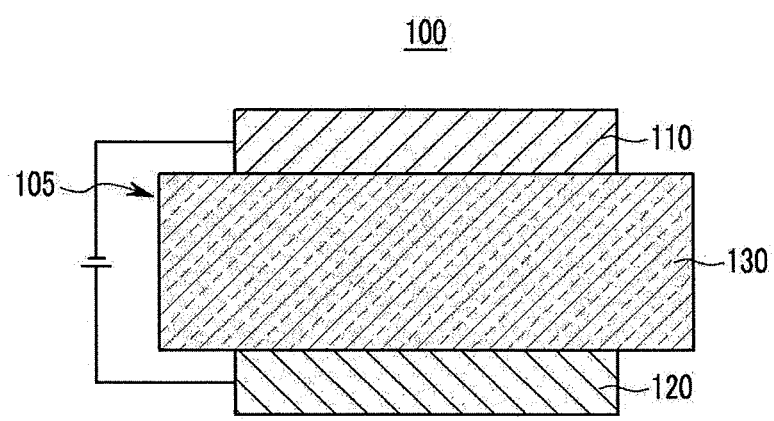
FIGS. 1 to 5 illustrate cross-sectional views showing organic light emitting diodes according to various embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, the term "substituted" refers to one substituted with deuterium, a halogen, a hydroxy group, an amino group, a substituted or unsubstituted C1 to C30 amine group, nitro group, a substituted or unsubstituted C1 to C40 silyl group, a C1 to C30 alkyl group, a C1 to C10 alkylsilyl group, C3 to C30 cycloalkyl group, a C6 to C30 aryl group, a C1 to C20 alkoxy group, a fluoro group, a C1 to C10 trifluoroalkyl group such as a trifluoromethyl group or the like, or a cyano group, replacing at least one hydrogen of a substituent or a compound.

In addition, two adjacent substituents of the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as a trifluoromethyl group and the like, or cyano group may be fused with each other to form a ring.

In the present specification, when specific definition is not otherwise provided, the term "hetero" refers to one including 1 to 3 hetero atoms selected from N, O, S, and P, and remaining carbons in one compound or substituent.

In the present specification, when a definition is not otherwise provided, the term "combination thereof" refers to at least two substituents bound to each other by a linker, or at least two substituents condensed to each other or mixed with each other.

As used herein, when a definition is not otherwise provided, the term "alkyl group" may refer to an aliphatic hydrocarbon group. The alkyl group may refer to "a saturated alkyl" without any double bond or triple bond.

The alkyl group may be a C1 to C20 alkyl group. For example, the alkyl group may be a C1 to C10 alkyl group or a C1 to C6 alkyl group. For example, a C1 to C4 alkyl group includes 1 to 4 carbon in an alkyl chain, and may be selected from methyl, ethyl, propyl, isopropyl, n-butyl, iso-butyl, sec-butyl, and t-butyl.

Specific examples of the alkyl group include a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, or the like.

As used herein, the term "aryl group" refers to a cyclic substituent in which all element of the cycle have p-orbitals that form conjugation. The aryl group may be a monocyclic or a fused ring polycyclic (i.e., rings sharing adjacent pairs of carbon atoms) functional group.

As used herein, the term "heteroaryl group" may refer to aryl group including 1 to 3 hetero atoms selected from N, O, S, and P, and a remainder being carbon in one functional group. The heteroaryl group may be a fused ring where each ring may include the 1 to 3 heteroatoms.

As examples, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

As used herein, hole characteristics refer to characteristics that hole formed in the anode is easily injected into the emission layer and transported in the emission layer due to conductive characteristics according to HOMO level. More specifically, it is similar to electron-repelling characteristics.

In addition, electron characteristics refer to characteristics that electron formed in the cathode is easily injected into the emission layer and transported in the emission layer due to conductive characteristics according to LUMO level. More specifically, it is similar to electron-withdrawing characteristics.

In an embodiment, a compound represented by the following Chemical Formula 1 is provided.

[Chemical Formula 1]

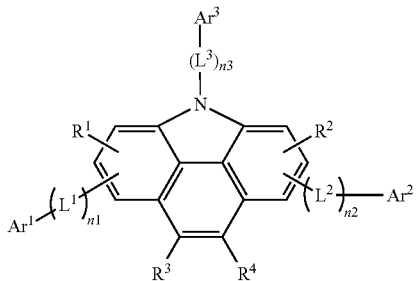

In the above Chemical Formula 1, $Ar^1$ and $Ar^2$ are each independently a substituted or unsubstituted C6 to C30 aryl group, or a substituted or unsubstituted C2 to C30 heteroaryl group, $R^1$ to $R^4$ and $Ar^3$ are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group, $L^1$ to $L^3$ are each independently a substituted or unsubstituted C6 to C30 arylene group or a substituted or unsubstituted C2 to C30 heteroarylene group, and n1 to n3 are independently integers of 0 to 3.

The compound according to this embodiment includes a condensation compound core as in the above Chemical Formula 1 and thus may have an improved glass transition temperature and crystallization properties.

The compound represented by the above Chemical Formula 1 may include various substituents and thus may have various energy bandgaps.

The compound may have an appropriate energy level depending on the substituents and thus, may fortify the hole transport characteristics or electron transport characteristics of an organic optoelectronic device and bring about excellent effects with respect to efficiency and driving voltage. Also, the compound may have excellent electrochemical and thermal stability and thus, improve life-span characteristics during the operation of the organic optoelectronic device.

For example, the compound may be represented by the following Chemical Formula 2.

[Chemical Formula 2]

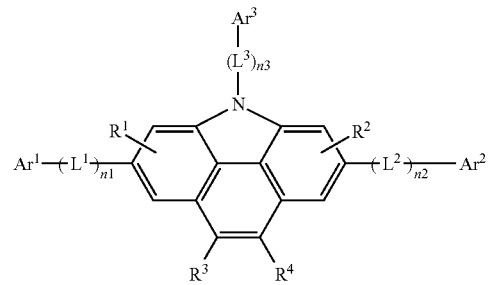

In the above Chemical Formula 2, $Ar^1$ and $Ar^2$ may each independently be a substituted or unsubstituted C6 to C30 aryl group, or a substituted or unsubstituted C2 to C30 heteroaryl group, $R^1$ to $R^4$ and $Ar^3$ may each independently be hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group, $L^1$ to $L^3$ may each independently be a substituted or unsubstituted C6 to C30 arylene group or a substituted or unsubstituted C2 to C30 heteroarylene group, and n1 to n3 may independently be integers of 0 to 3.

The structure of the above Chemical Formula 2 is an example of the above Chemical Formula 1 in which some of the substituents are limited with respect to position.

As examples, $Ar^1$ and $Ar^2$ may each independently be a substituted or unsubstituted C6 to C30 aryl group.

As examples, $Ar^1$ and $Ar^2$ may each independently be a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group.

In other implementations, at least one of $Ar^1$ and $Ar^2$ may be a substituted or unsubstituted dibenzofuranyl group, a substituted or unsubstituted dibenzothiophenyl group, a substituted or unsubstituted carbazolyl group, or a substituted or unsubstituted fluorenyl group.

Hole and/or electron characteristics of the compound may be appropriately adjusted.

As examples, at least one of $Ar^1$ and $Ar^2$ may be a substituent represented by the following Chemical Formula 3 or 4.

[Chemical Formula 3]

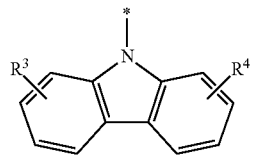

[Chemical Formula 4]

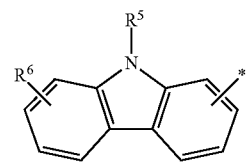

In the above Chemical Formulae 3 and 4, $R^3$ to $R^6$ may each independently be hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group.

In addition, $L^1$ to $L^3$ may be selectively adjusted to determine a conjugation length of the compound. Thus, a triplet energy bandgap may be adjusted based on the adjustment of $L^1$ to $L^3$. Accordingly, desired characteristics of a material in an organic optoelectronic device may be provided. In addition, the triplet energy bandgap may be adjusted by changing bonding positions among ortho, para, and meta positions.

$L^1$ and $L^2$ may each be a substituted or unsubstituted C6 to C30 arylene group. The compound may have appropriate hole and electron characteristics.

Examples of $L^1$ and $L^2$ include a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluorenylene group, a substituted or unsubstituted p-terphenyl group, a substituted or unsubstituted m-terphenyl group, a substituted or unsubstituted perylenyl group, or the like.

$Ar^3$ may be a substituted or unsubstituted phenyl group, or a substituted or unsubstituted biphenyl group, as examples.

At least one of $Ar^1$ or $Ar^2$ may be a silyl group, a cyano group, deuterium, a halogen, or a C6 to C30 aryl group substituted with a C1 to 10 alkyl group, as examples.

Examples of the compound according to one embodiment may be as follows.

1

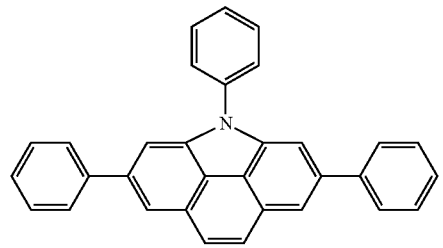

2

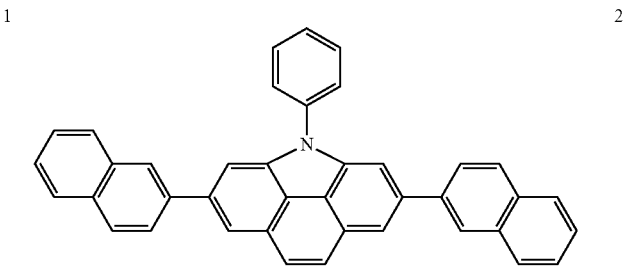

3

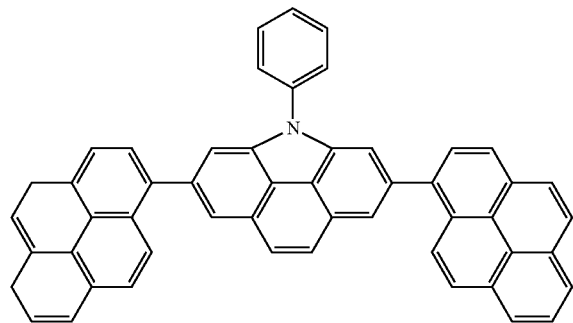

4

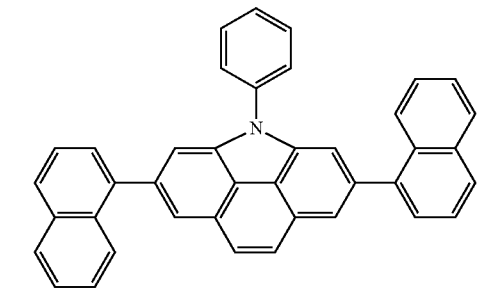

5

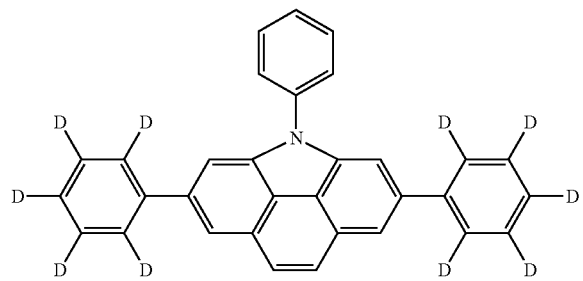

6

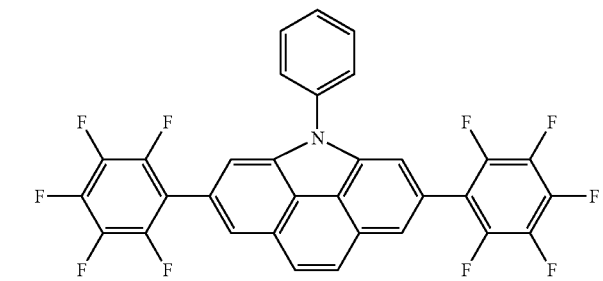

7
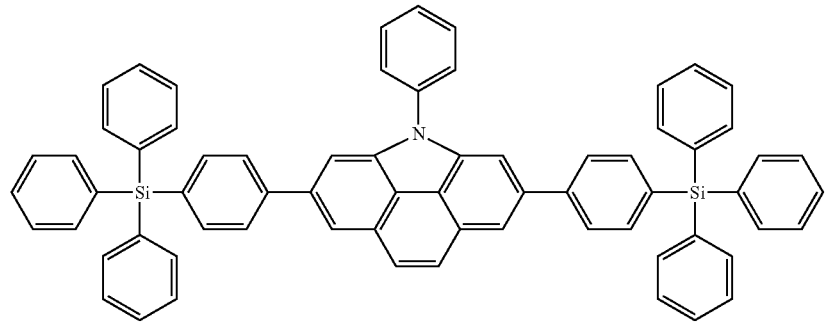
8
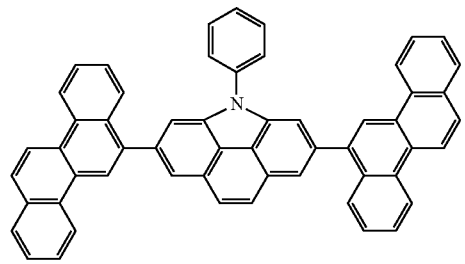
9
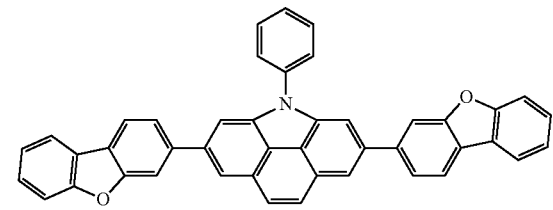
10
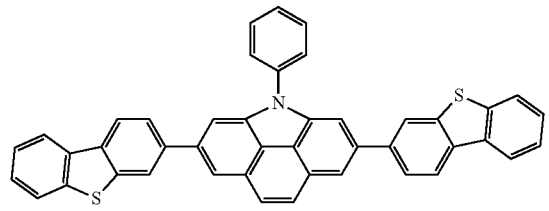
11
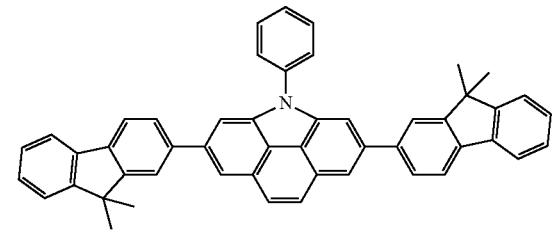
12
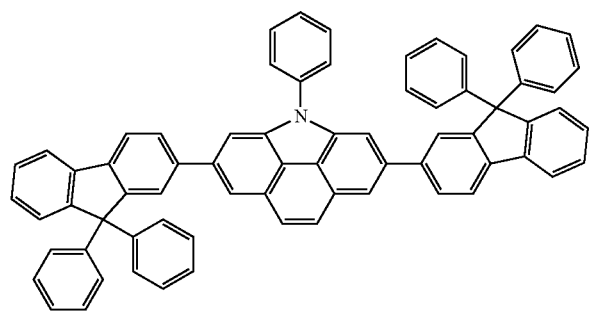
13
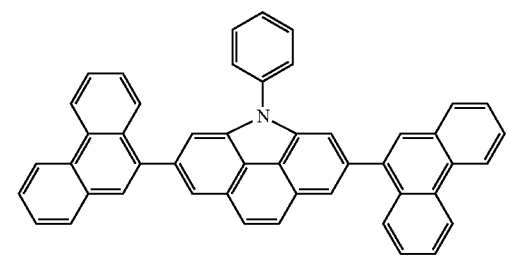
14
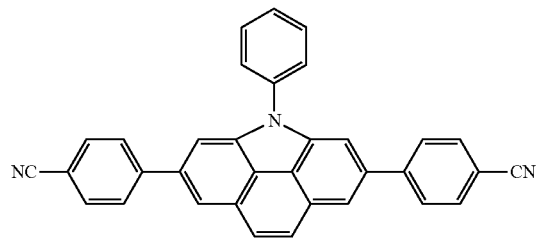
15
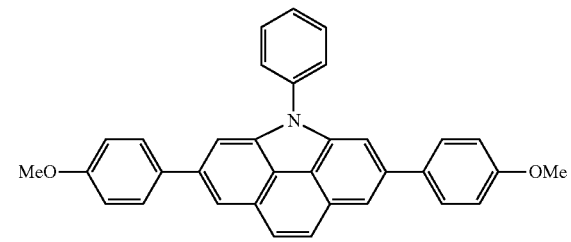

-continued
16
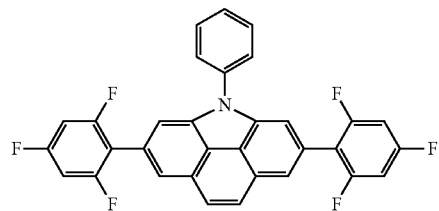
17
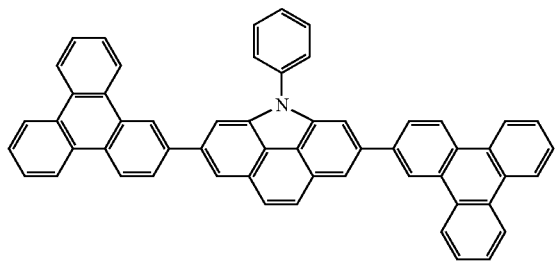
18
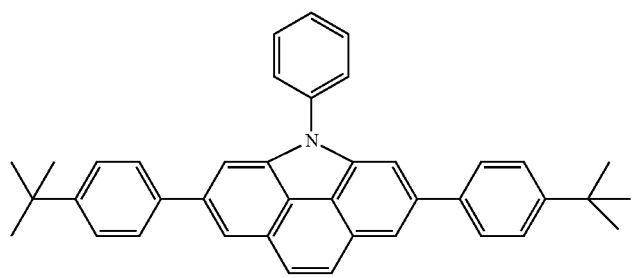
19
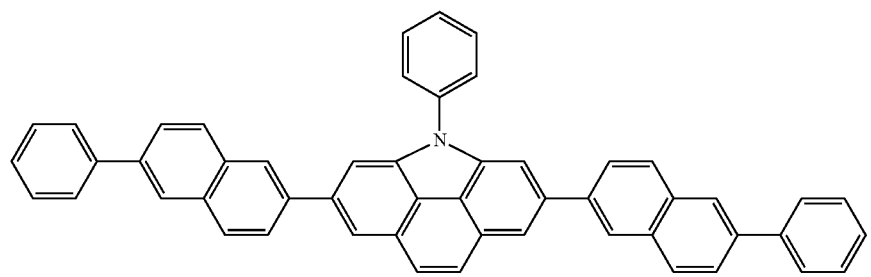
20
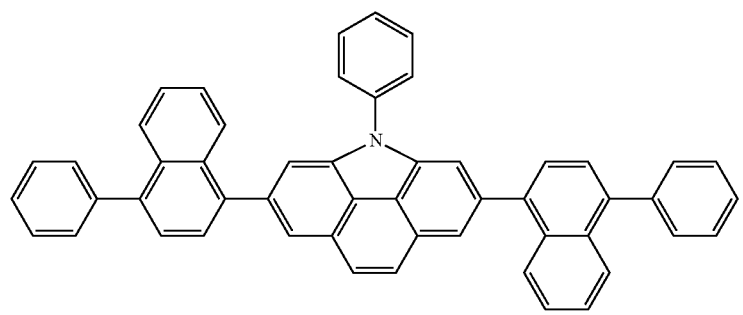
21
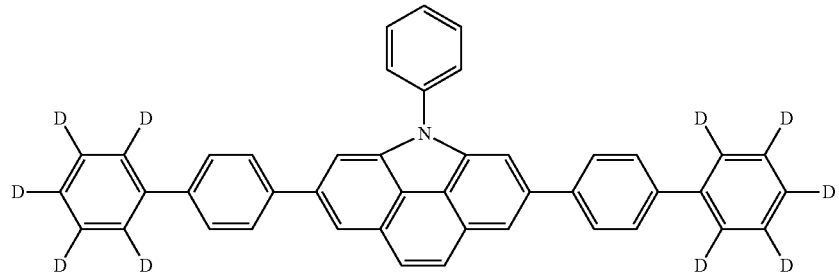

-continued
22
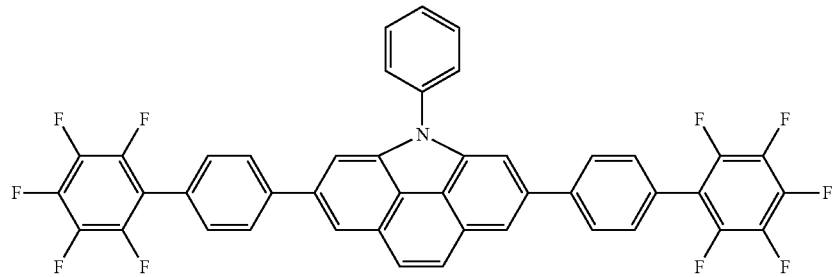
23
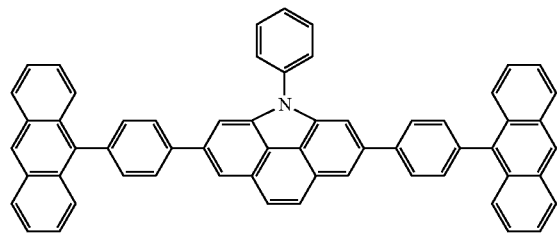
24
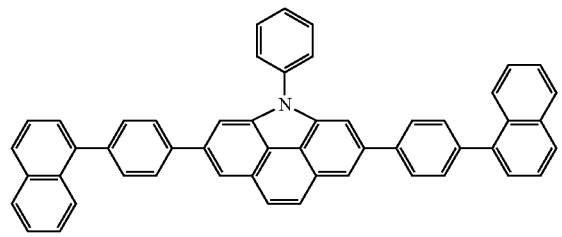
25
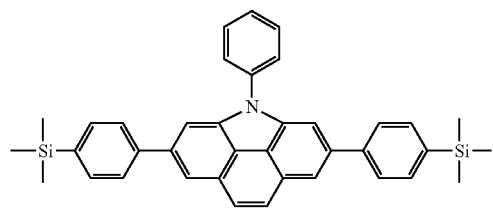
26
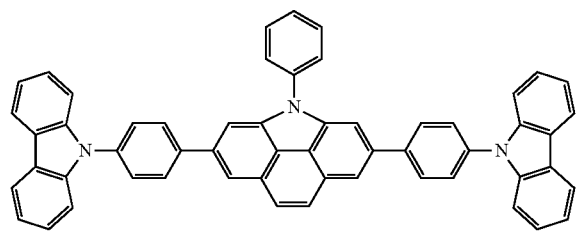
27
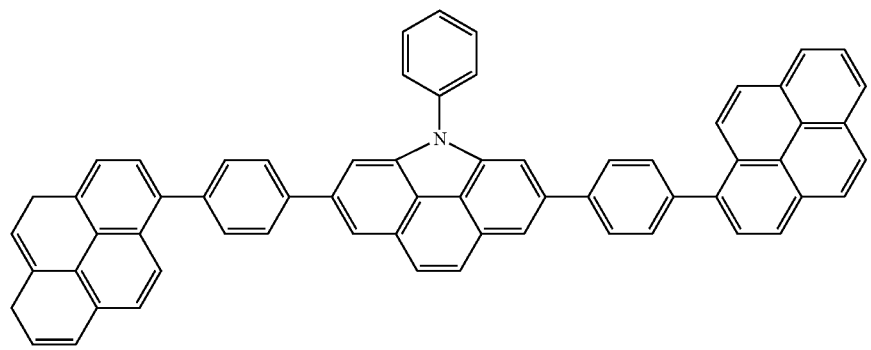
28
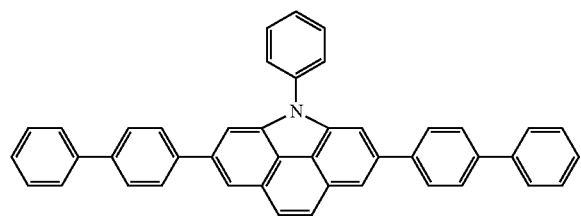
29
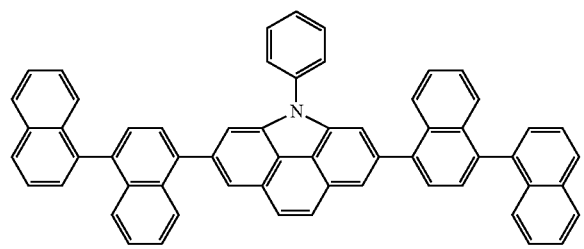

-continued
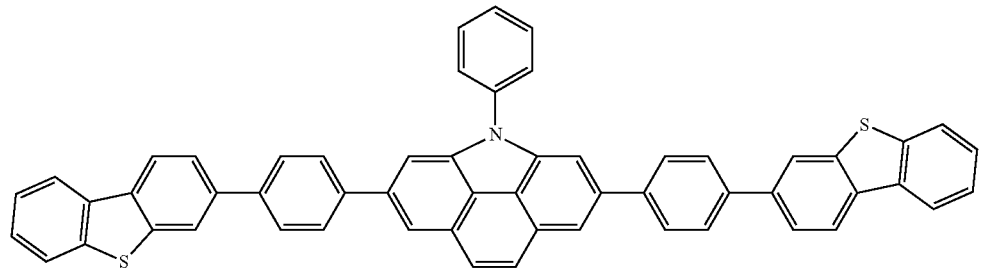
30
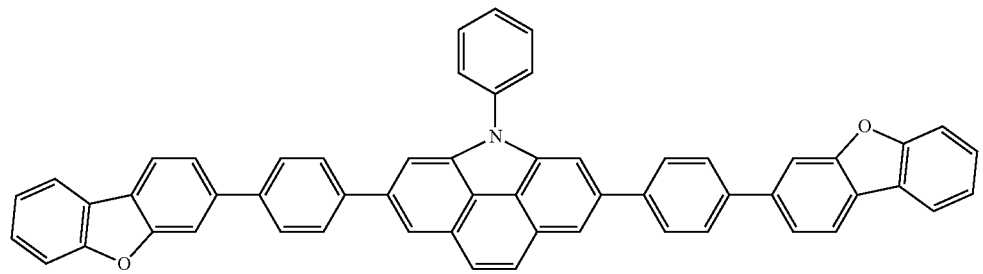
31
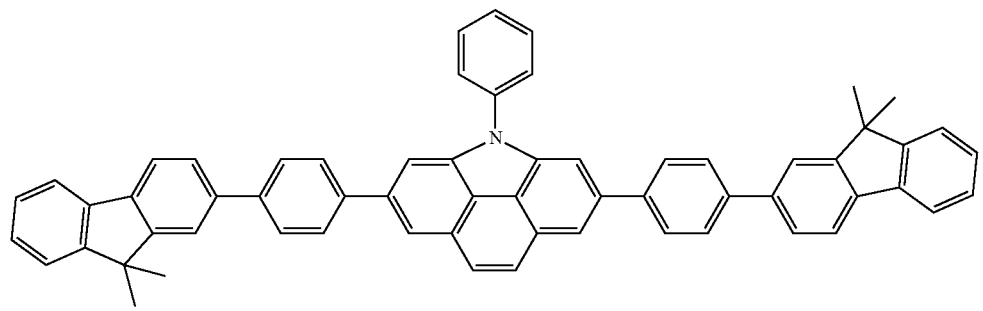
32
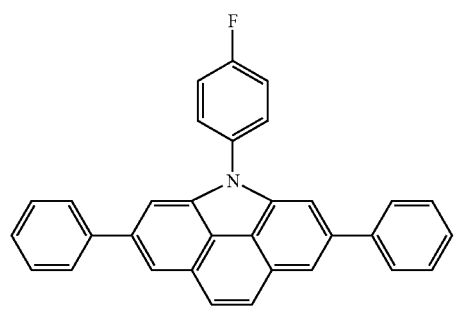
33
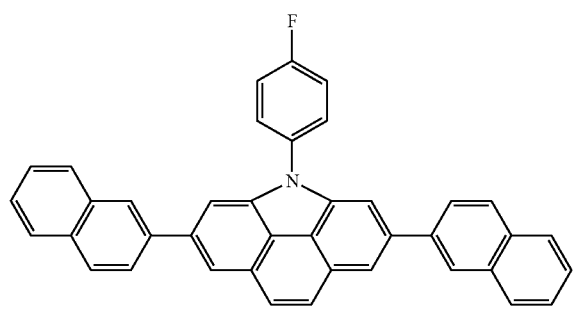
34
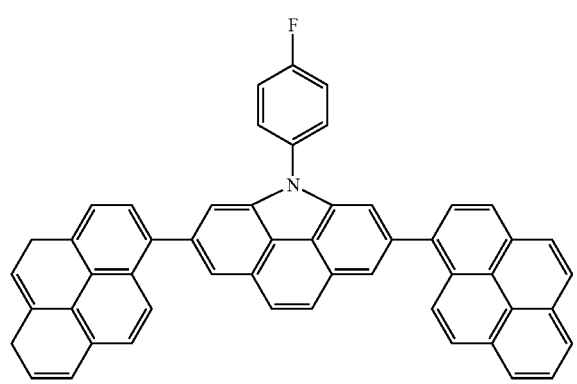
35
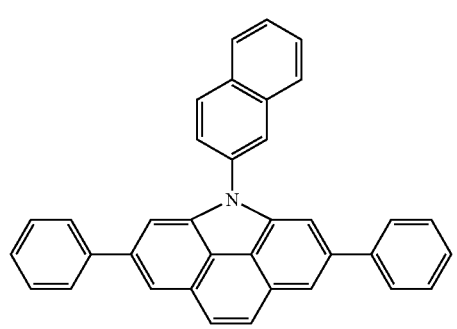
36

-continued
37 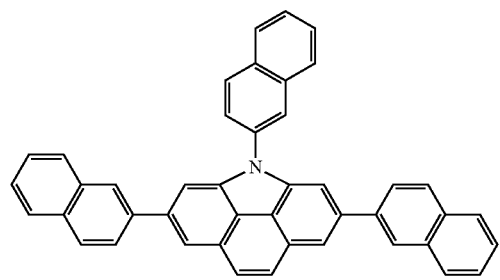
38 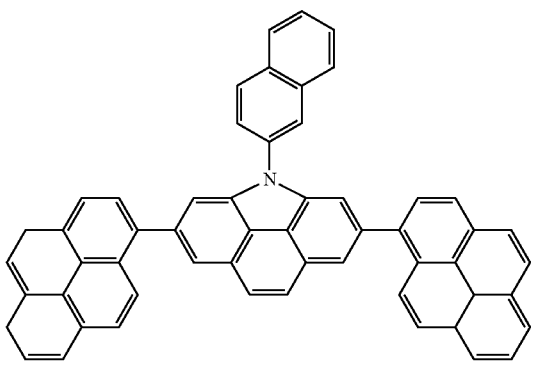
39 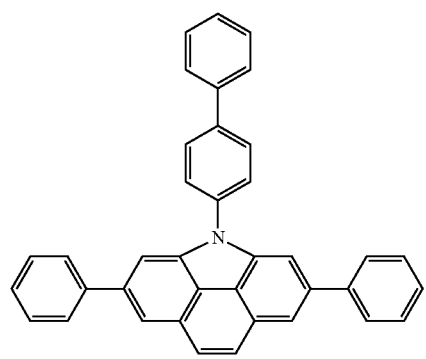
40 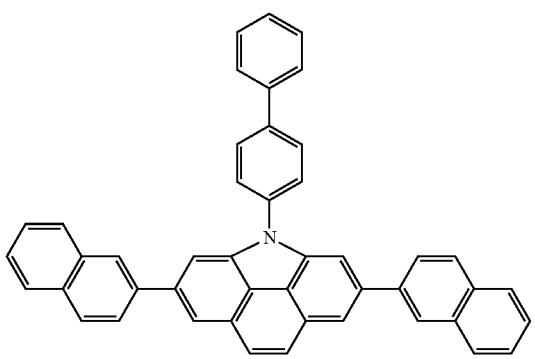
41 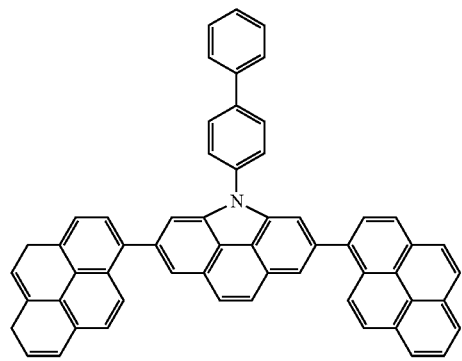
42 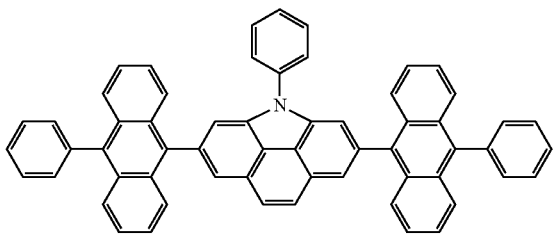
43 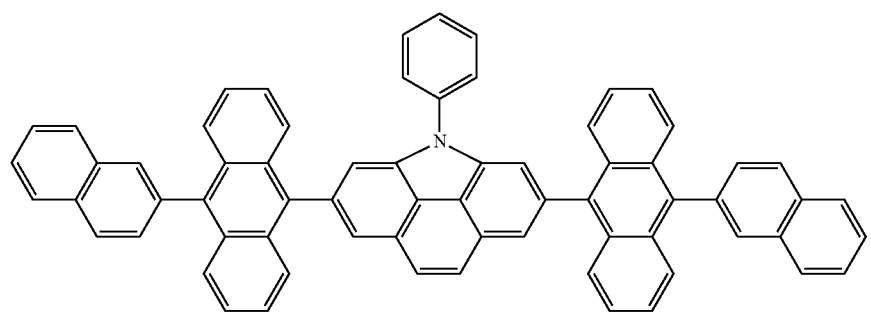

44
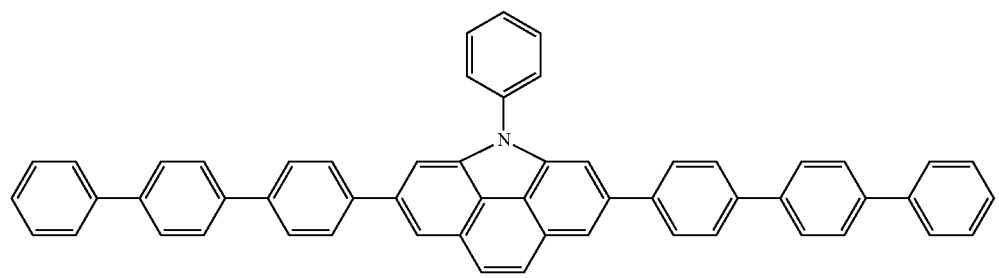
45
46
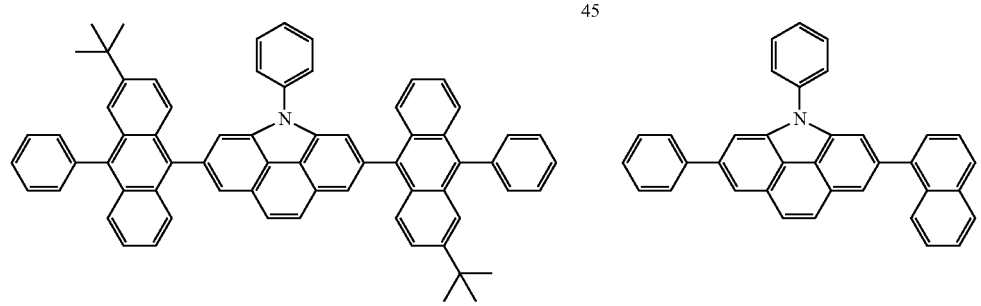
47
48
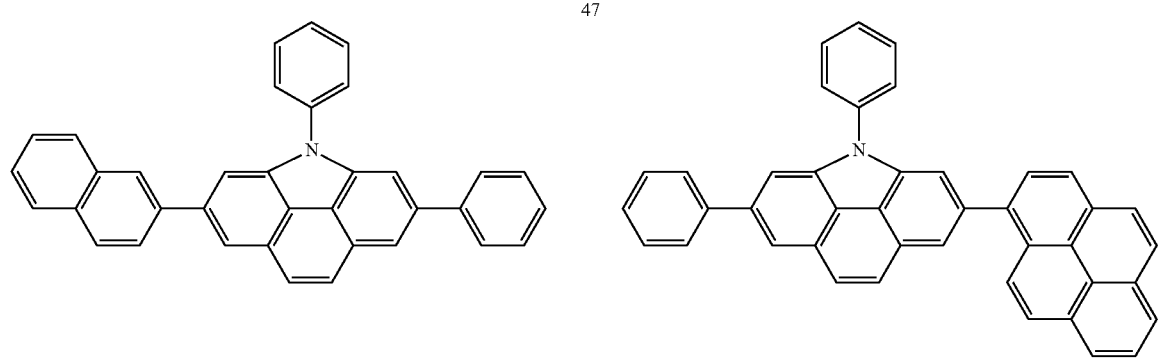
49
50
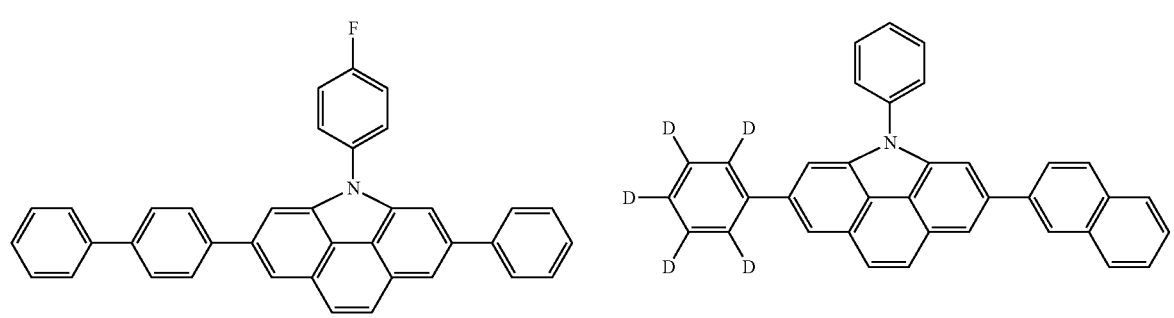
51
52
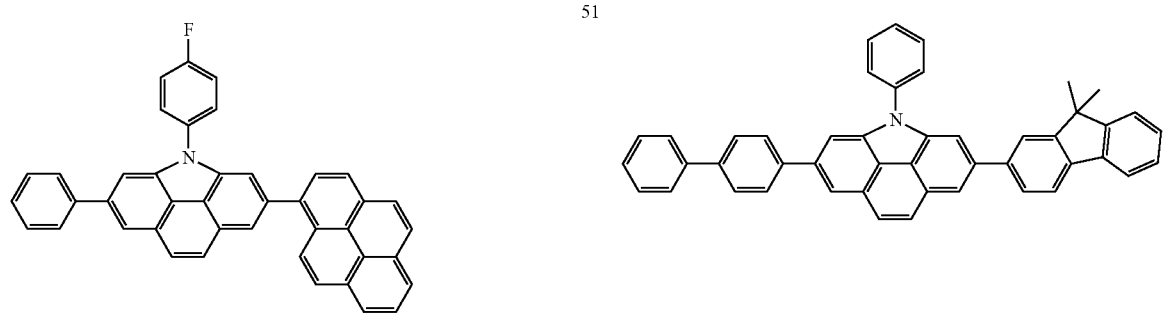

-continued
53
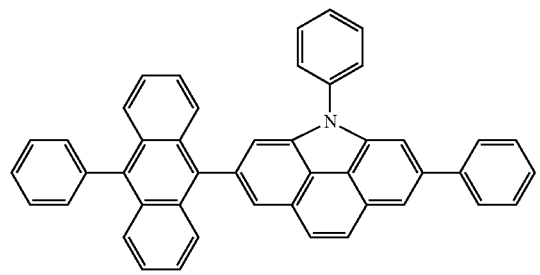
54
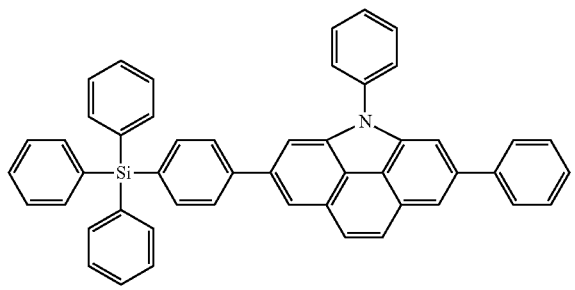
55
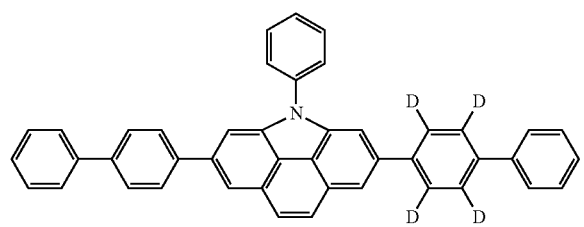
56
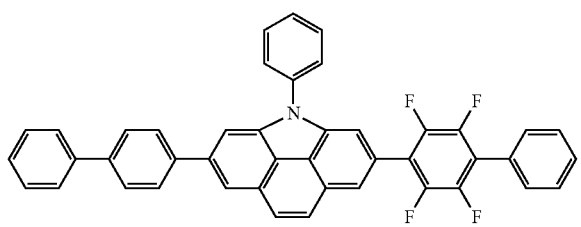
57
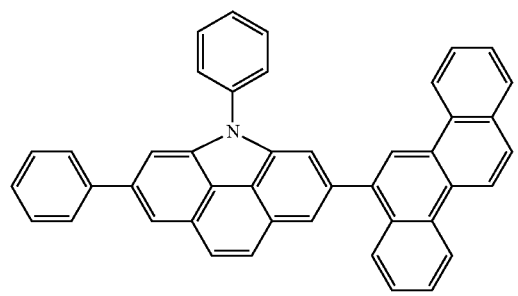
58
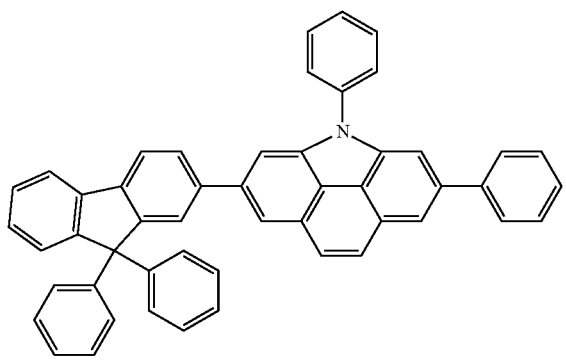
59
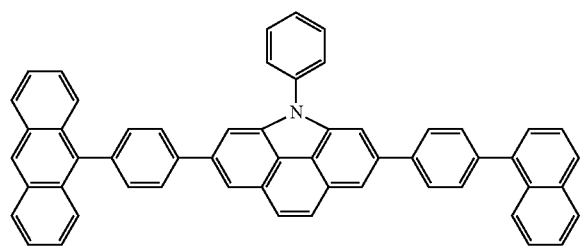
60
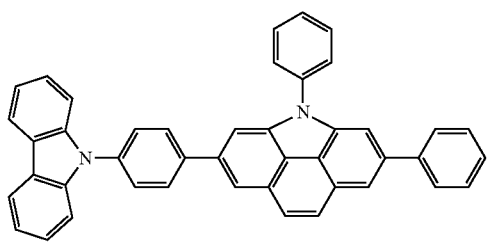
61
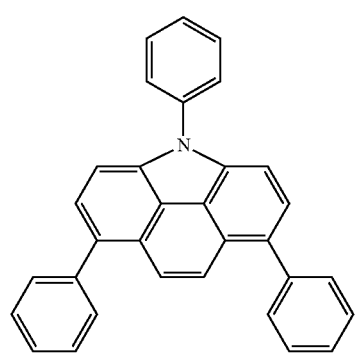
62
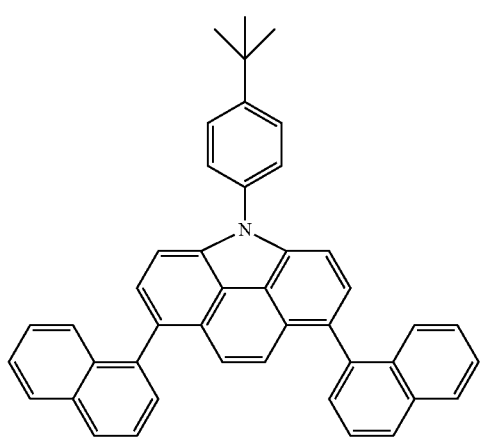

-continued
63
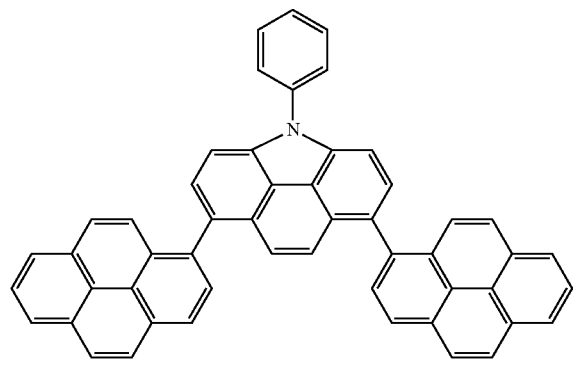
64
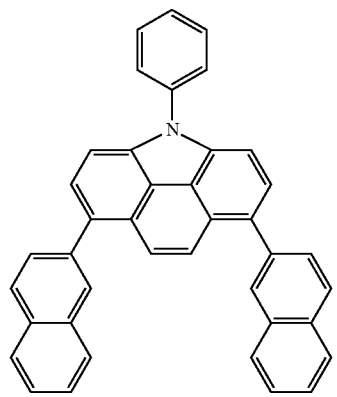
65
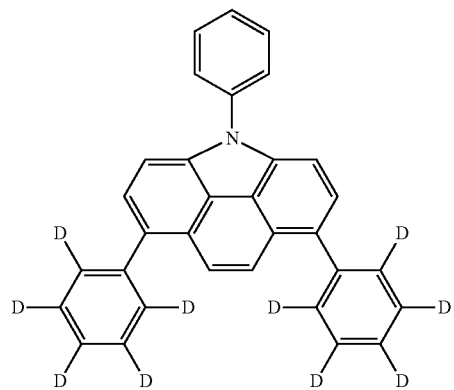
66
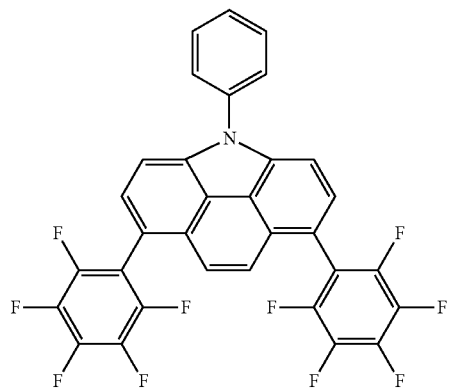
67
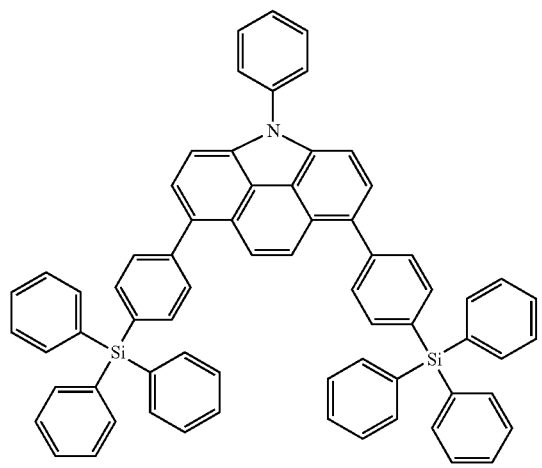
68
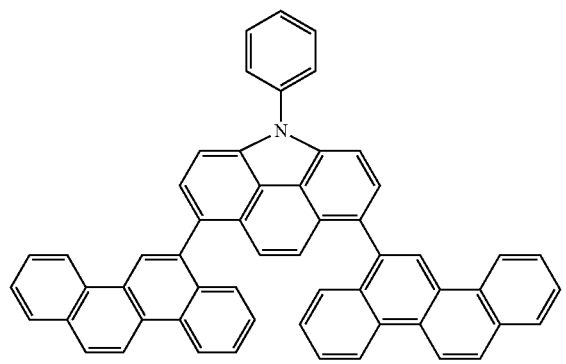

-continued
| 69 | 70 |
|---|---|
| 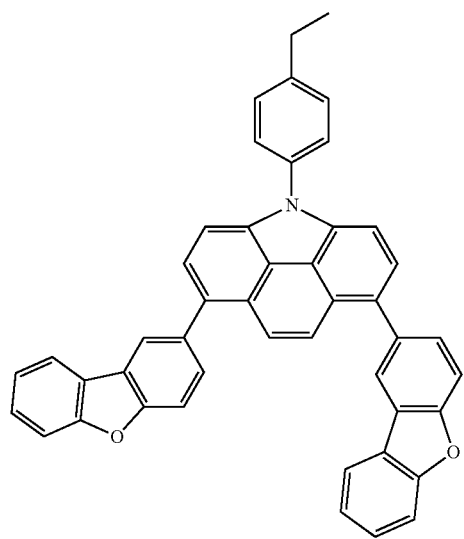 | 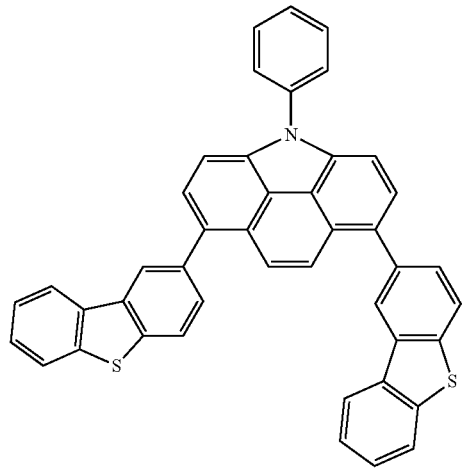 |
| 71 | 72 |
| 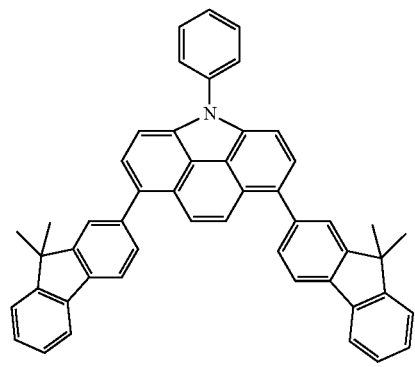 | 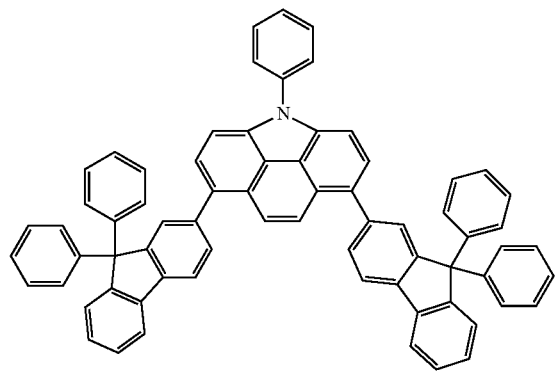 |
| 73 | 74 |
| 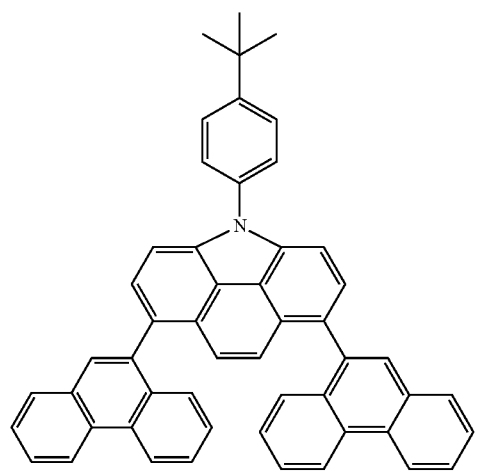 | 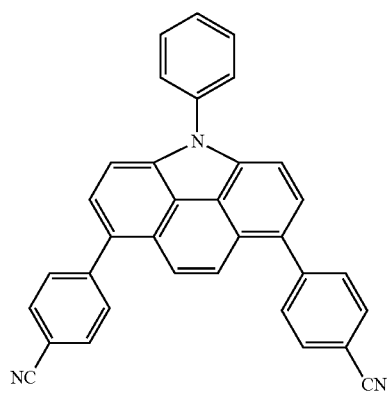 |

-continued
75
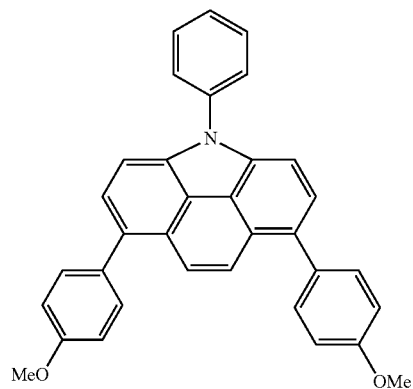
76
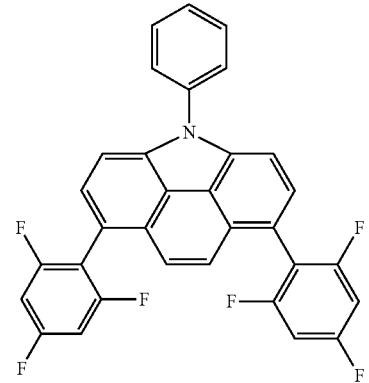
77
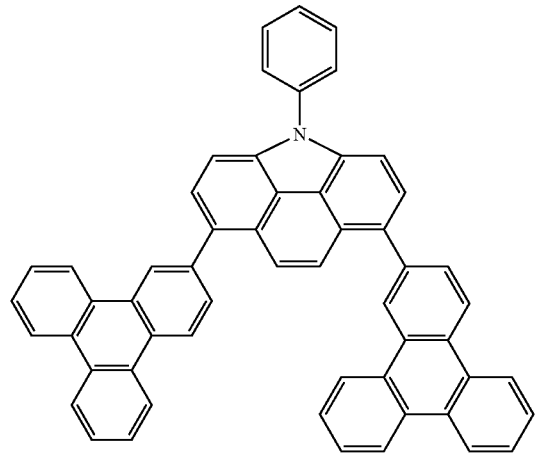
78
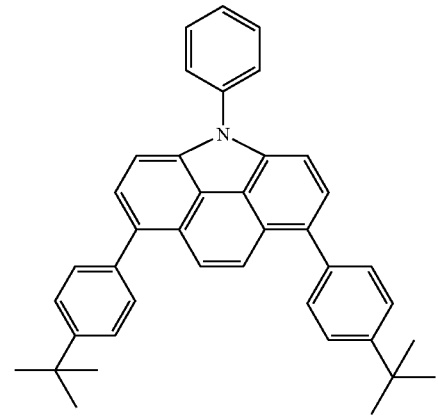
79
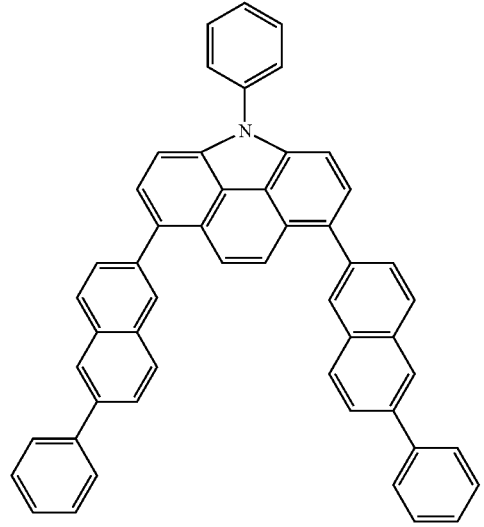
80
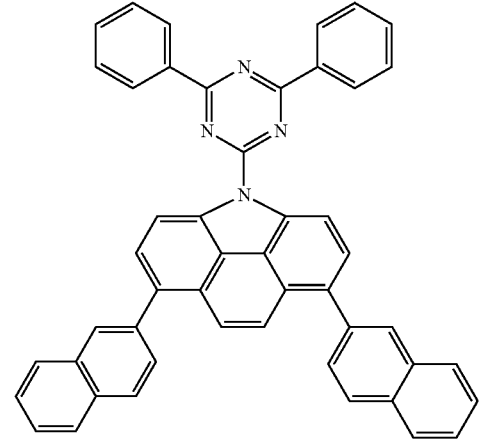

-continued
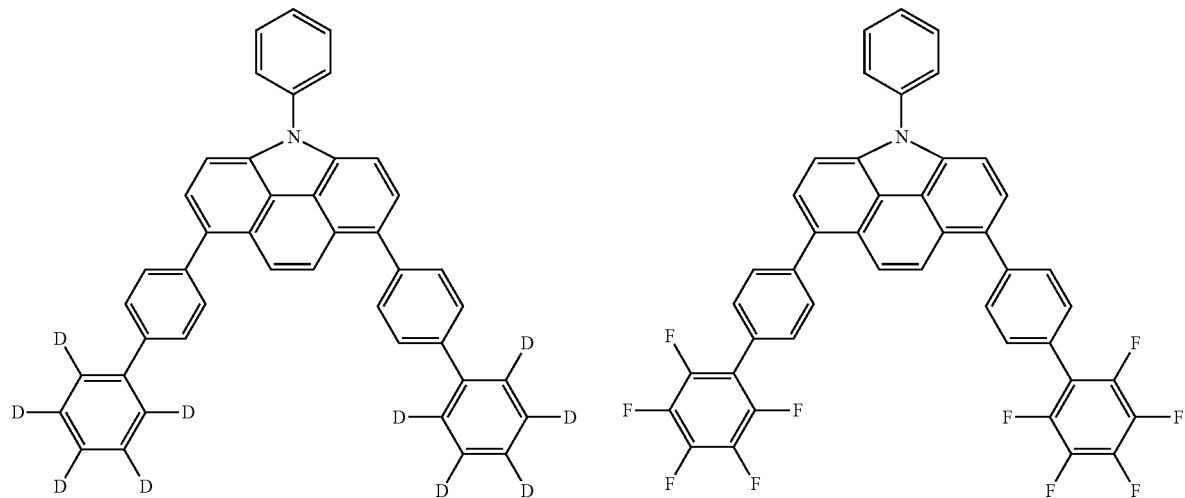
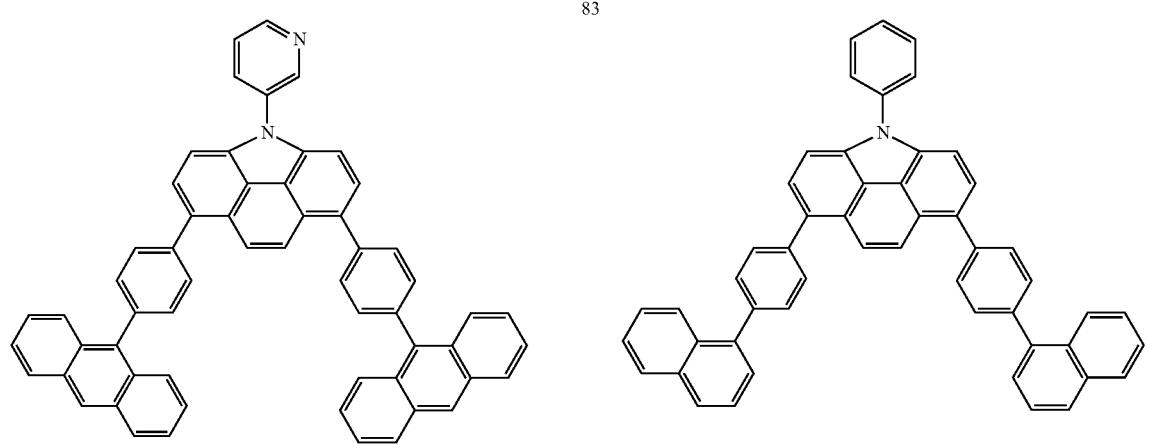
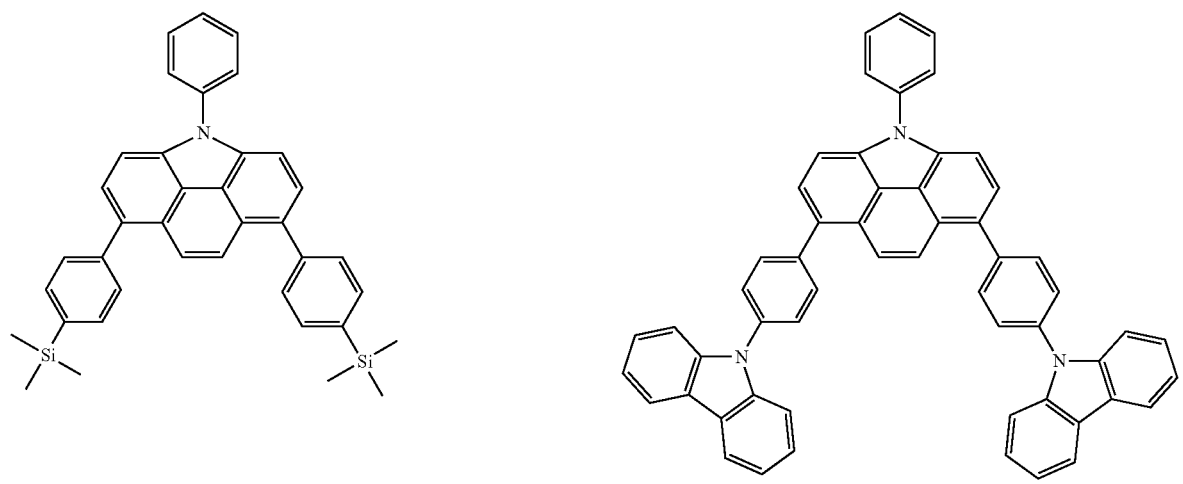

87
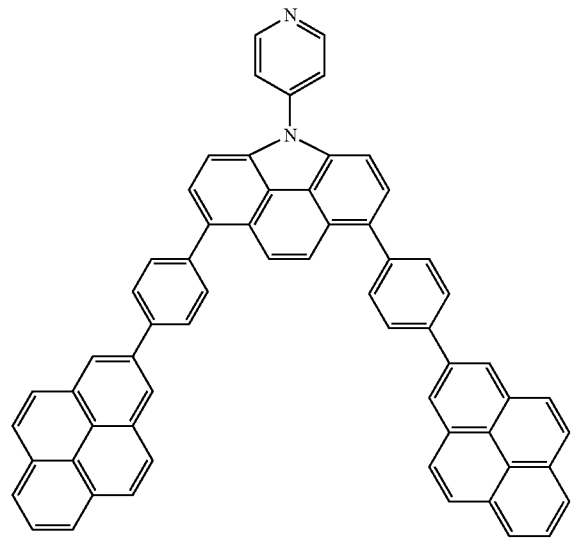
88
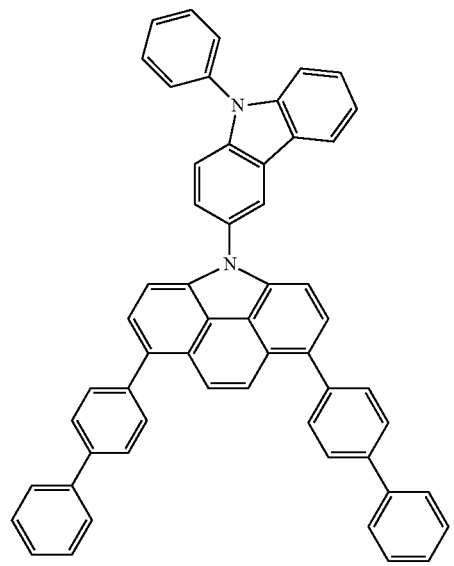
89
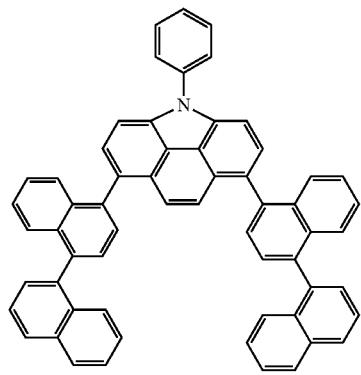
90
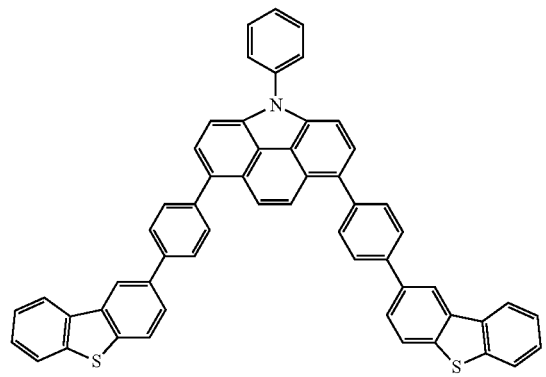
91
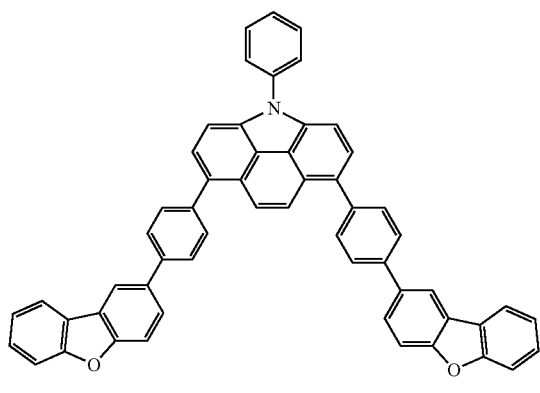
92
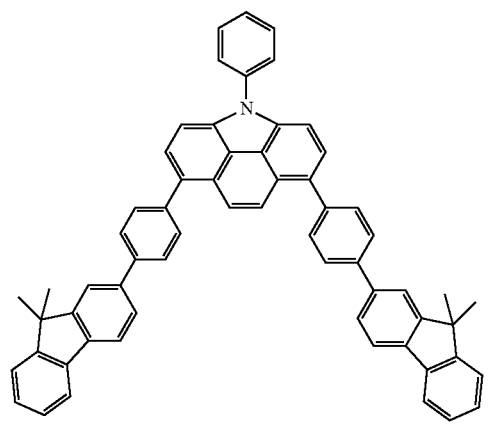

93
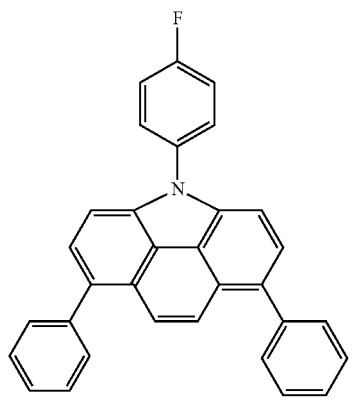
94
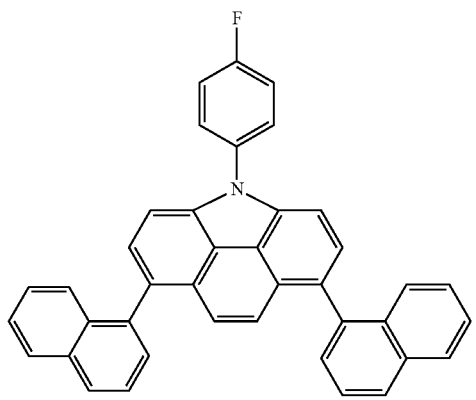
95
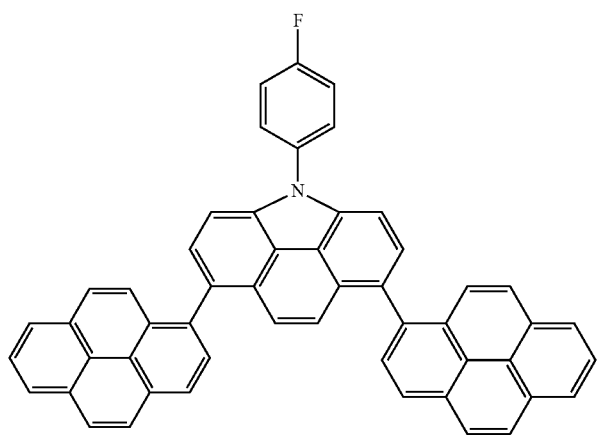
96
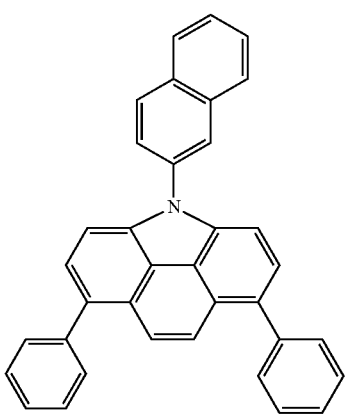
97
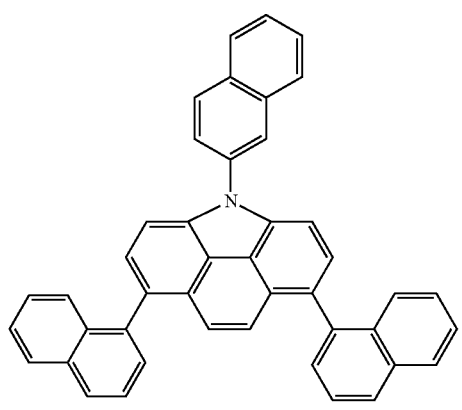
98
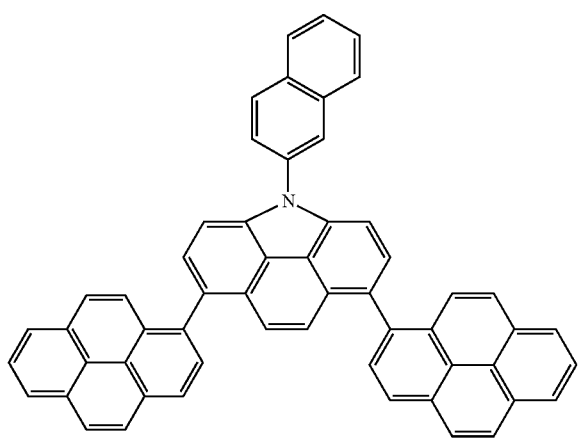

99
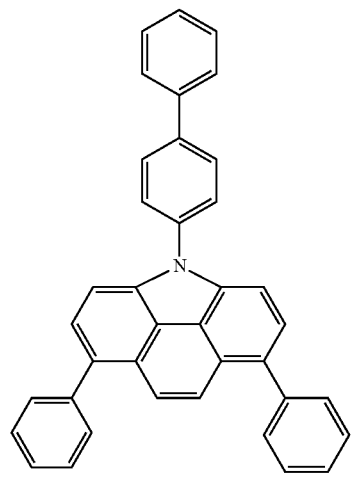
100
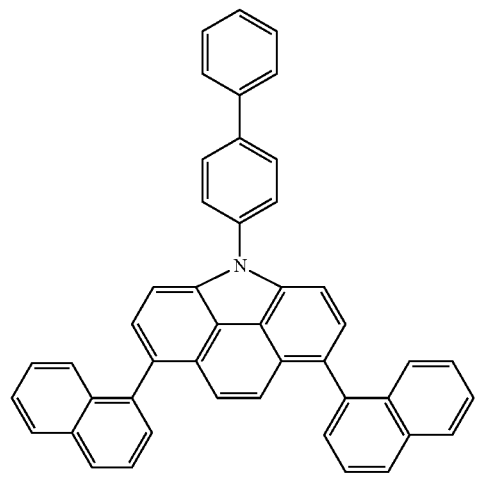
101
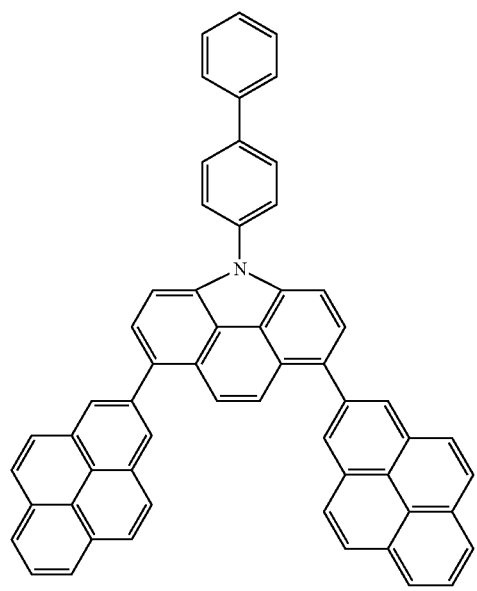
102
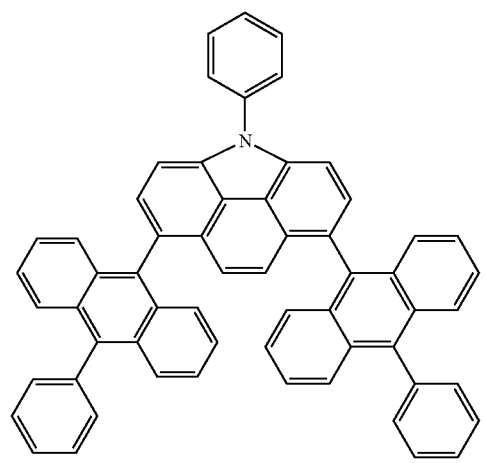
103
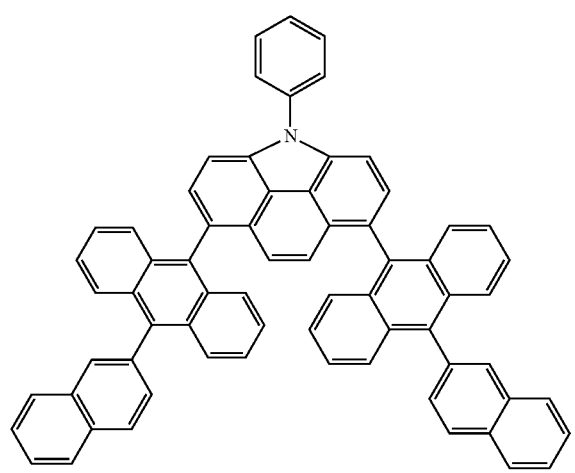
104
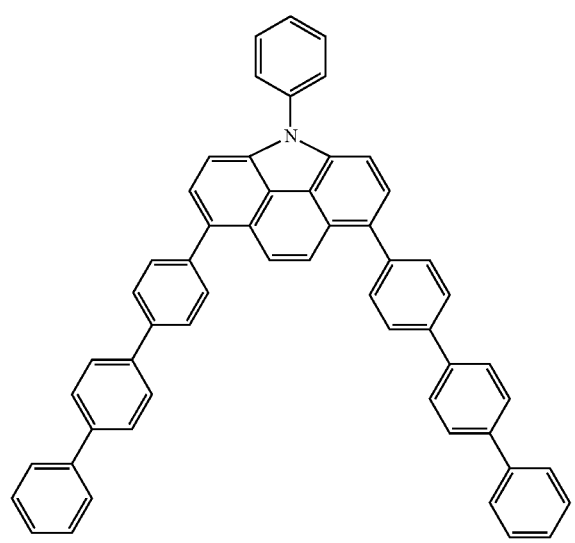

-continued
105
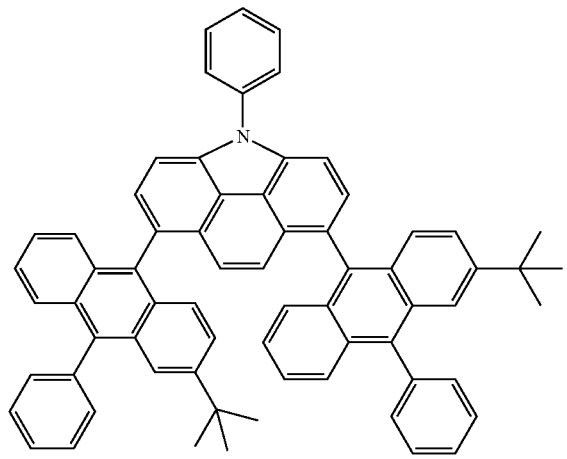
106
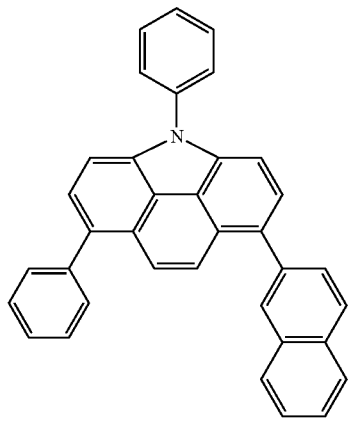
107
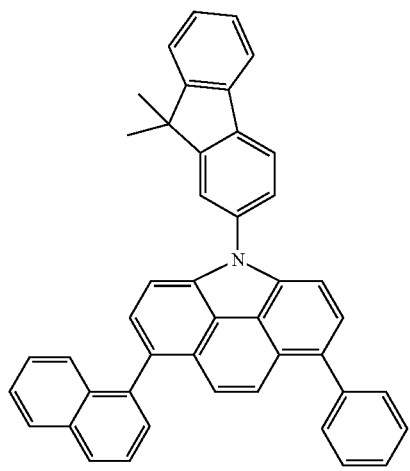
108
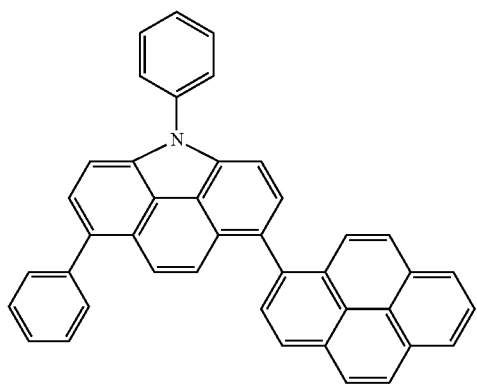
109
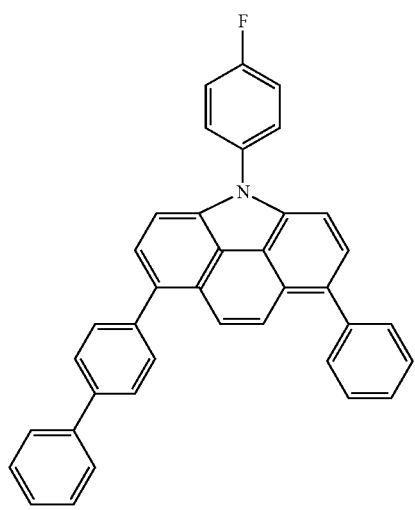
110
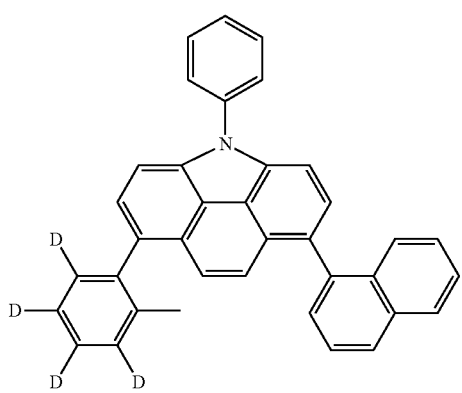

-continued
111
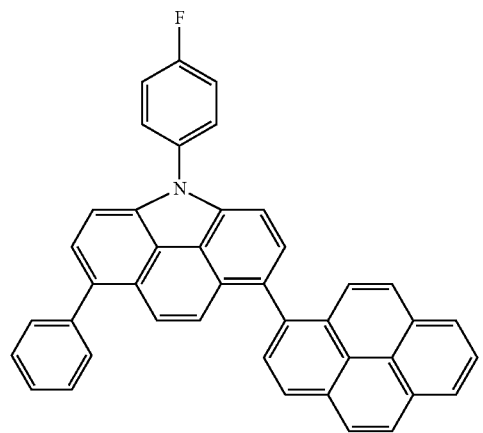
112
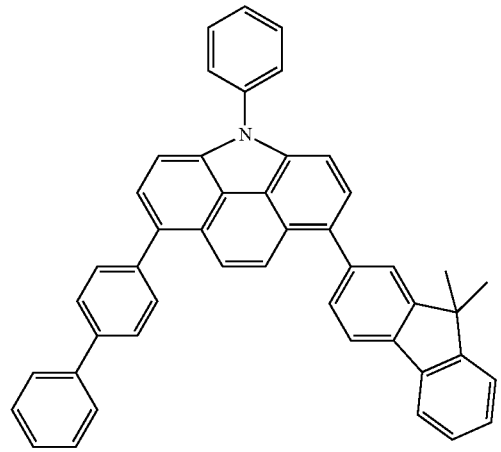
113
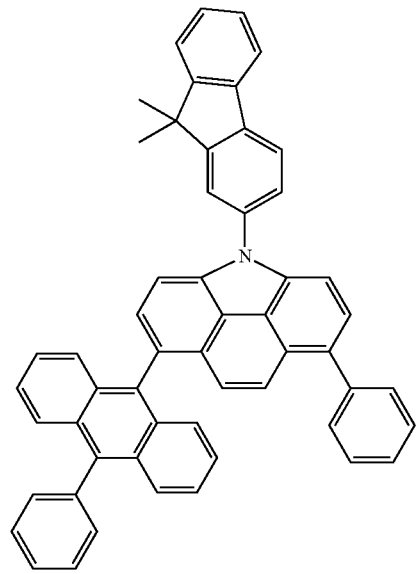
114
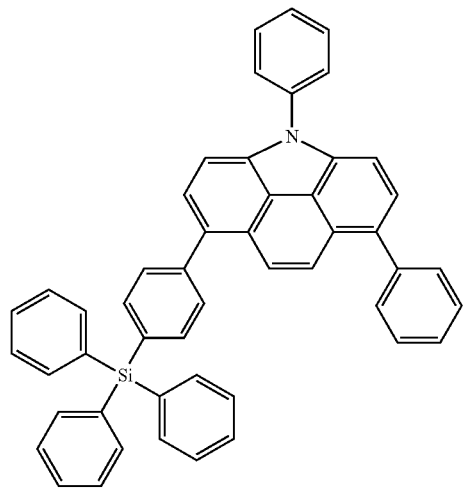
115
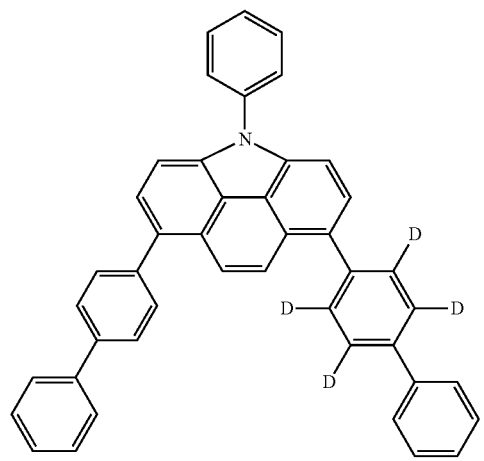
116
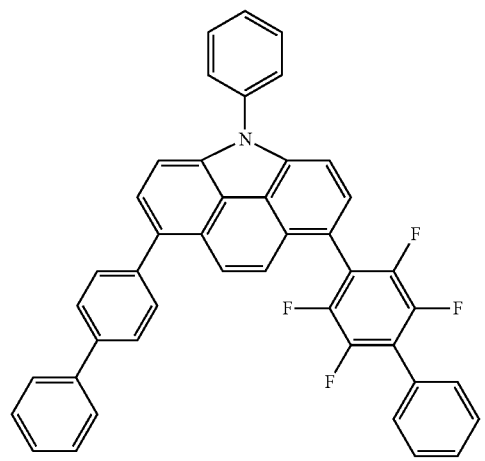

117

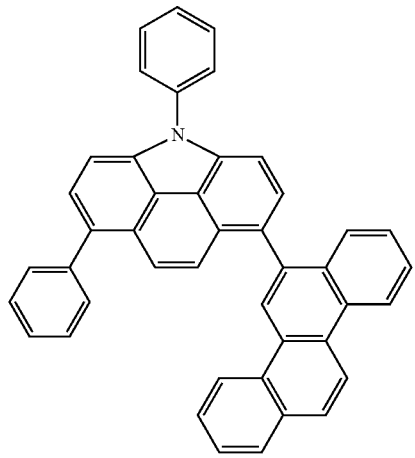

118

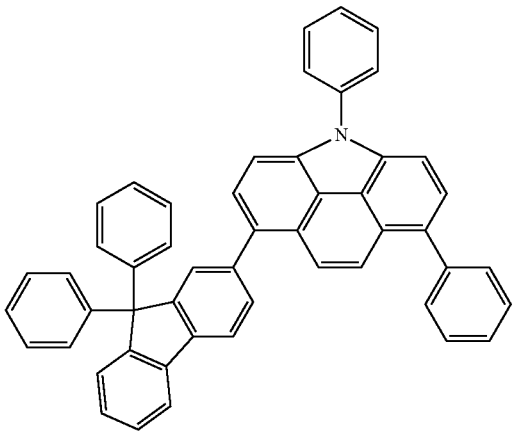

119

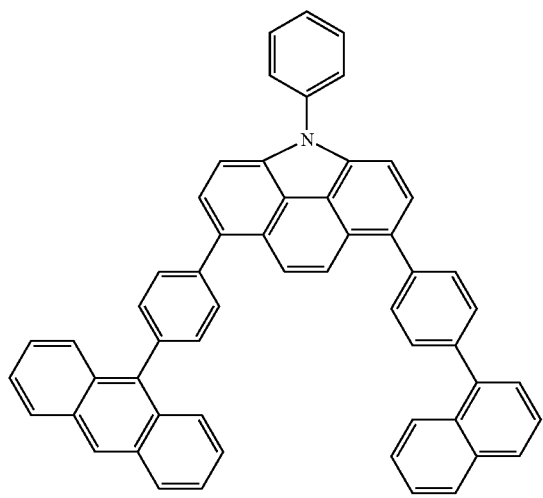

120

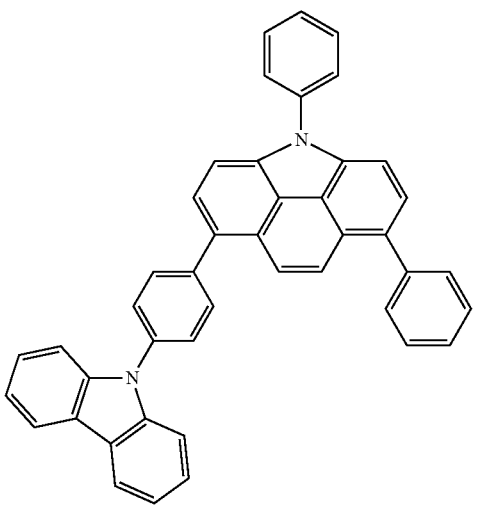

In another embodiment, an organic optoelectronic device may include an anode, a cathode, and at least one organic thin layer between the anode and the cathode. The at least one of the organic thin layers may include the compound for an organic optoelectronic device according to embodiments.

The compound for an organic optoelectronic device may be used in an organic thin layer and thus improves life-span characteristics, efficiency characteristic, electrochemical stability, and thermal stability of an organic optoelectronic device, and may lower a driving voltage.

The organic thin layer may be an emission layer.

The organic optoelectronic device may be an organic light emitting diode, an organic photoelectric device, an organic solar cell, an organic transistor, an organic photo-conductor drum, or an organic memory device.

For example, the organic optoelectronic device may be an organic light emitting diode. FIGS. 1 to 5 illustrate cross-sectional views showing organic light emitting diodes including the compound for an organic optoelectronic device according to one embodiment.

Referring to FIGS. 1 to 5, organic light emitting diodes 100, 200, 300, 400, and 500 according to embodiments include at least one organic thin layer 105 interposed between an anode 120 and a cathode 110.

The anode 120 may include an anode material having a large work function to assist with hole injection into an organic thin layer. The anode material may include: a metal such as nickel, platinum, vanadium, chromium, copper, zinc, or gold, or alloys thereof; a metal oxide such as zinc oxide, indium oxide, indium tin oxide (ITO), or indium zinc oxide (IZO); a bonded metal and oxide such as ZnO:Al or $SnO_2$:Sb; or a conductive polymer such as poly(3-methylthiophene), poly[3,4-(ethylene-1,2-dioxy)thiophene] (PEDT), polypyrrole, and polyaniline, as examples. For example, the anode 120 may be a transparent electrode including indium tin oxide (ITO).

The cathode 110 may include a cathode material having a small work function to assist with electron injection into an organic thin layer. The cathode material may include: a metal such as magnesium, calcium, sodium, potassium, titanium, indium, yttrium, lithium, gadolinium, aluminum, silver, tin, or lead, or alloys thereof, or a multi-layered material such as LiF/Al, Liq/Al, $LiO_2$/Al, LiF/Ca, LiF/Al, or $BaF_2$/Ca, as examples. For example, the cathode 120 may be a metal electrode including aluminum.

Referring to FIG. 1, the organic light emitting diode 100 may include an organic thin layer 105 including only an emission layer 130.

Figure 2:
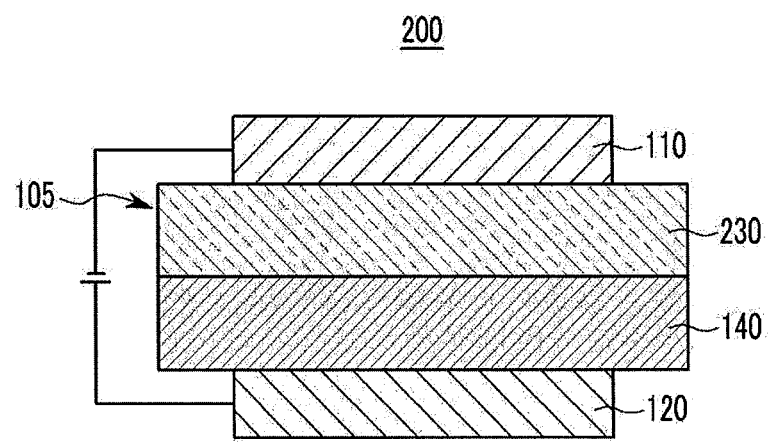

Referring to FIG. 2, a double-layered organic light emitting diode 200 may include an organic thin layer 105 including an emission layer 230 including an electron transport layer (ETL), and a hole transport layer (HTL) 140. As shown in FIG. 2, the organic thin layer 105 may include a double layer of the emission layer 230 and hole transport layer (HTL) 140. The emission layer 130 may also function as an electron transport layer (ETL). The hole transport layer (HTL) 140 layer may have an excellent binding property with a transparent electrode such as ITO or an excellent hole transport capability.

Figure 3:
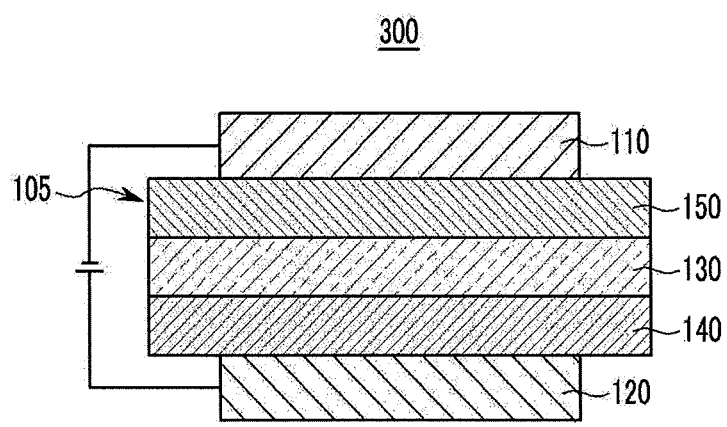

Referring to FIG. 3, a three-layered organic light emitting diode 300 may include an organic thin layer 105 including an electron transport layer (ETL) 150, an emission layer 130, and a hole transport layer (HTL) 140. The emission layer 130 may be independently installed, and layers having an excellent electron transport capability or an excellent hole transport capability may be separately stacked.

Figure 4:
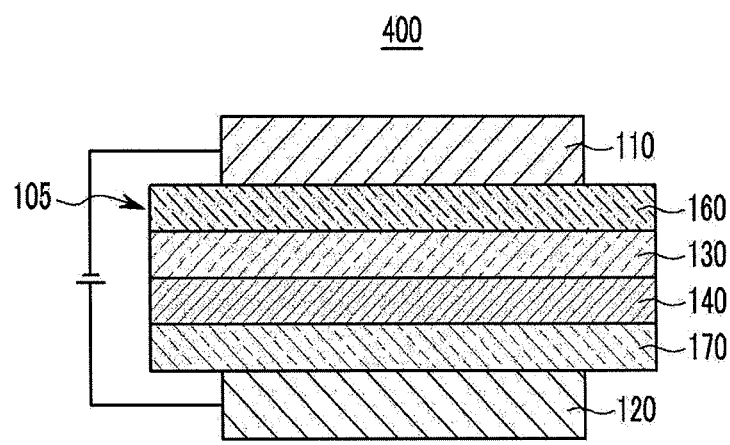

As shown in FIG. 4, a four-layered organic light emitting diode 400 may include an organic thin layer 105 including an electron injection layer (EIL) 160, an emission layer 130, a hole transport layer (HTL) 140, and a hole injection layer (HIL) 170 for adherence with the cathode of ITO.

Figure 5:
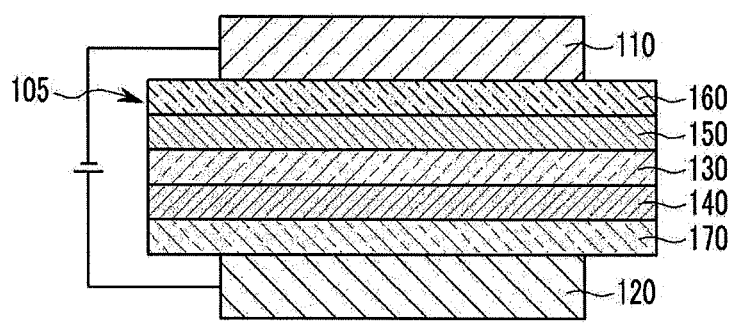

As shown in FIG. 5, a five layered organic light emitting diode 500 may include an organic thin layer 105 including an electron transport layer (ETL) 150, an emission layer 130, a hole transport layer (HTL) 140, and a hole injection layer (HIL) 170, and may further include an electron injection layer (EIL) 160 to achieve a low voltage.

In FIGS. 1 to 5, the organic thin layer 105 including at least one selected from an electron transport layer (ETL) 150, an electron injection layer (EIL) 160, emission layers 130 and 230, a hole transport layer (HTL) 140, a hole injection layer (HIL) 170, or combinations thereof, may include a compound for an organic optoelectronic device according to embodiments.

Particularly, the compound may be used in the emission layers 130 and 230, and may be used as a green phosphorescent dopant material in the emission layers.

The organic light emitting diode may be manufactured by forming an anode on a substrate, forming an organic thin layer using a dry coating method such as evaporation, sputtering, plasma plating, and ion plating, or a wet coating method such as spin coating, dipping, and flow coating, and providing a cathode thereon.

Another embodiment provides a display device including the organic photoelectric device according to the above embodiment.

Hereinafter, the embodiments are illustrated in more detail with reference to examples.

Preparation of Compound for Organic Optoelectronic Device

Synthesis Example 1

Synthesis of Compound 1

[Reaction Scheme 1]

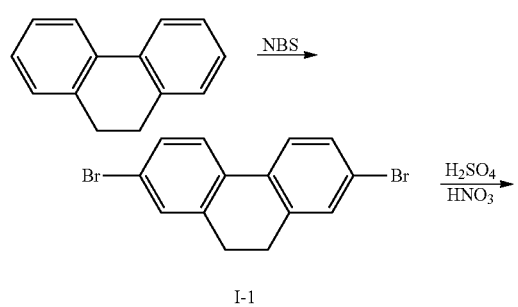

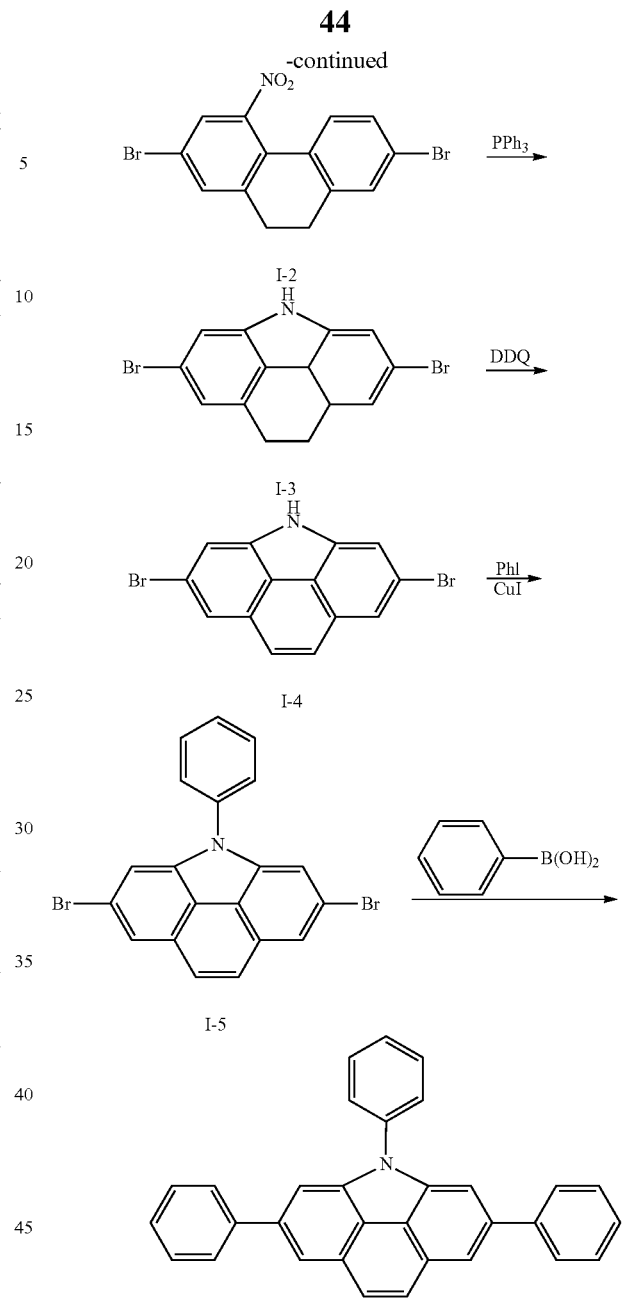

Synthesis of Intermediate I-1

10.0 g (55.4 mmol) of 9,10-dihydrophenanthrene, 21.8 g (121.0 mmol) of N-bromosuccinimide, and 0.5 g (2.7 mmol) of p-TsOH were dissolved in 30 mL of acetonitrile, and the solution was agitated at 50° C. for 12 hours. The reaction solution was cooled down to room temperature and then, agitated for 30 minutes to extract a crystal. The crystal was collected by using a pressure-reducing filter and was washed with methanol, obtaining 8.4 g of a grey intermediate I-1 (45% of a yield). The produced compound was examined through LC-MS. $C_{14}H_{10}Br_2$ $M^+$ 335.9

Synthesis of Intermediate I-2

5.0 g (15.0 mmol) of the intermediate I-1 was completely dissolved in 50 mL of dichloromethane, 1.7 g (30.0 mmol)

of nitric acid was added thereto at room temperature, then, 1.5 g (15.0 mmol) of sulfuric acid was slowly added in a dropwise fashion, and the mixture was agitated at 30° C. for 6 hours. When the reaction was complete, the reactant was cooled down to room temperature and cooled down, 50 mL of methanol was added thereto, and the mixture was agitated for 2 hours, extracting a crystal. The crystal was collected by using a pressure-reducing filter and washed with methanol, obtaining 5.2 g of a yellow crystal intermediate I-2 (90% of a yield). The produced compound was examined through LC-MS. $C_{14}H_9Br_2NO_2$ $M^+$ 380.9

Synthesis of Intermediate I-3

4.6 g (12.0 mmol) of the intermediate I-2 was dissolved in 30 mL of o-dichlorobenzene, the solution was heated for complete dissolution, 4.7 g (18.0 mmol) of triphenylphosphine was added thereto, and the mixture was agitated at 180° C. for 3 hours. The reaction solution was cooled down to room temperature, and a remnant obtained by evaporating a solvent therein was separated and purified through silica gel column chromatography and washed with methanol, obtaining 2.9 g of a white crystal intermediate I-3 (70% of a yield). The produced compound was examined through LC-MS. $C_{14}H_{11}Br_2N$ $M^+$ 350.9

Synthesis of Intermediate I-4

10 g (10.0 mmol) of the intermediate I-3 was dissolved in 100 ml of toluene under an oxygen atmosphere, 0.6 g (0.3 mmol) of 2,3-dichloro-5,6-dicyano-1,4-benzoquinone and 0.2 g (0.3 mmol) of $NaNO_2$ were added thereto at room temperature, and the mixture was agitated at 110° C. for 6 hours. When the reaction was complete, the reaction solution was cooled down to room temperature, and a remnant obtained by evaporating a solvent therein was separated and purified through silica gel column chromatography, obtaining 3.1 g of an intermediate I-4 (90% of a yield). The produced compound was examined through LC-MS. $C_{14}H_7Br_2N$ $M^+$ 346.8

Synthesis of Intermediate I-5

3.4 g (10.0 mmol) of the intermediate I-4, 2.5 g (12.0 mmol) of iodobenzene, 0.2 g (1.0 mmol) of 1,10-phenanthroline, 0.2 g (2.0 mmol) of CuI, and 4.1 g (30.0 mmol) of $K_2CO_3$ were dissolved in 30 mL of DMF (N,N-dimethylformamide), and the solution was agitated at 80° C. for 24 hours. The reaction solution was cooled down to room temperature and three times extracted with 30 mL of water and 40 mL of diethylether. The collected organic layer was dried with magnesium sulfate, and a remnant obtained by evaporating a solvent therein was separated and purified through silica gel column chromatography, obtaining 3.8 g of an intermediate I-5 (89% of a yield). The produced compound was examined through LC-MS. $C_{20}H_{11}Br_2N$ $M^+$ 422.9

Synthesis of Compound 1

2.5 g (5.0 mmol) of the intermediate I-5, 1.3 g (11.0 mmol) of phenylboronic acid, 0.58 g (0.5 mmol) of $Pd(PPh_3)_4$ and 2.1 g (15.0 mmol) of $K_2CO_3$ were dissolved in 40 mL of THF/$H_2O$ mixed in a volume ratio of 2/1, and the solution was agitated at 80° C. for 5 hours. The reaction solution was cooled down to room temperature and three times extracted with 30 mL of water and 30 mL of diethylether. The collected organic layer was dried with magnesium sulfate, and a remnant obtained by evaporating a solvent therein was separated and purified through silica gel column chromatography, obtaining 1.4 g of a compound 1 (67% of a yield). The produced compound was examined through MS/FAB and $^1$HNMR. $C_{32}H_{21}N$ cal. 419.17. found 420.17. $^1$H NMR (CDCl$_3$, 400 MHz) δ 8.02 (m, 2H), 7.87-7.84 (s, 4H), 7.93-7.88 (m, 2H), 7.86 (m, 2H), 7.84-7.80 (m, 4H), 7.77-7.65 (m, 5H), 7.59 (d, 2H).

Synthesis Example 2

Synthesis of Compound 46

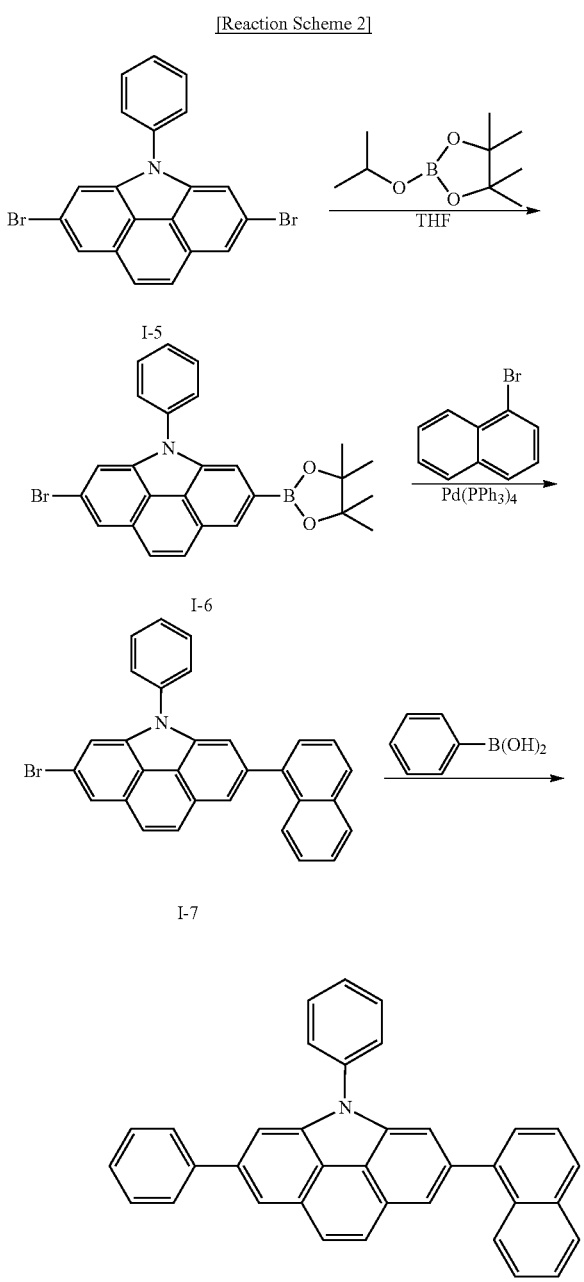

[Reaction Scheme 2]

46

Synthesis of Intermediate I-6

10.0 g (23.6 mmol) of the intermediate I-5 was dissolved in 100 ml of THF, and 10 mL of n-BuLi (25.0 mmol, 2.5M in hexane) was slowly added thereto in a dropwise fashion at −78° C. The mixture was agitated at the same temperature for 1 hour, 9.3 mL (50.0 mmol) of 2-isoproxy-4,4,5,5,-tetramethyl-1,3,2-dioxaborolane was slowly added thereto in a dropwise fashion, and the reaction solution was agitated at −78° C. for 1 hour and additionally agitated at room temperature for 24 hours. When the reaction was complete, 50 mL of a 10% HCl aqueous solution and 50 mL of $H_2O$ were added thereto, and the mixture was three times extracted with 80 mL of diethylether. The collected organic layer was dried with magnesium sulfate, and a remnant obtained by evaporating a solvent therein was separated and purified through silica gel column chromatography, obtaining 8.1 g of an intermediate I-6 (73% of a yield). The compound was examined through LC-MS. $C_{26}H_{23}BBrNO_2$: $M^+$ 471.1

Synthesis of Intermediate I-7

4.7 g (10.0 mmol) of the intermediate I-6, 2.7 g (13.0 mmol) of 1-bromo-naphthalene, 0.58 g (0.5 mmol) of $Pd(PPh_3)_4$, and 2.1 g (15.0 mmol) of $K_2CO_3$ were dissolved in 40 mL of $THF/H_2O$ mixed in a volume ratio of 2/1, and the solution was agitated at 80° C. for 5 hours. The reaction solution was cooled down to room temperature, 40 mL of water was added thereto, and the mixture was three times extracted with 50 mL of diethylether. The collected organic layer was dried with magnesium sulfate, and a remnant obtained by evaporating a solvent therein was separated and purified through silica gel column chromatography, obtaining 3.4 g of an intermediate I-7 (72% of a yield). The produced compound was examined through LC-MS. $C_{30}H_{18}BrN$ $M^+$ 472.1

Synthesis of Compound 46

1.9 g of a compound 46 (82% of a yield) was obtained according to the same method as the compound 1 was synthesized except for using the intermediate I-7 instead of the intermediate I-5. The produced compound was examined through MS/FAB and $^1H$ NMR. $C_{36}H_{23}N$ cal. 469.18. found 470.18. $^1H$ NMR ($CDCl_3$, 400 MHz) δ 8.17 (m, 1H), 8.02 (m, 1H), 7.92-7.84 (m, 4H), 7.76-7.74 (m, 1H), 7.63-7.35 (m, 13H), 7.29 (d, 1H), 7.25-7.13 (m, 2H).

Synthesis Example 3

Synthesis of Compound 61

[Reaction Scheme 3]

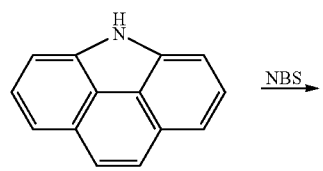

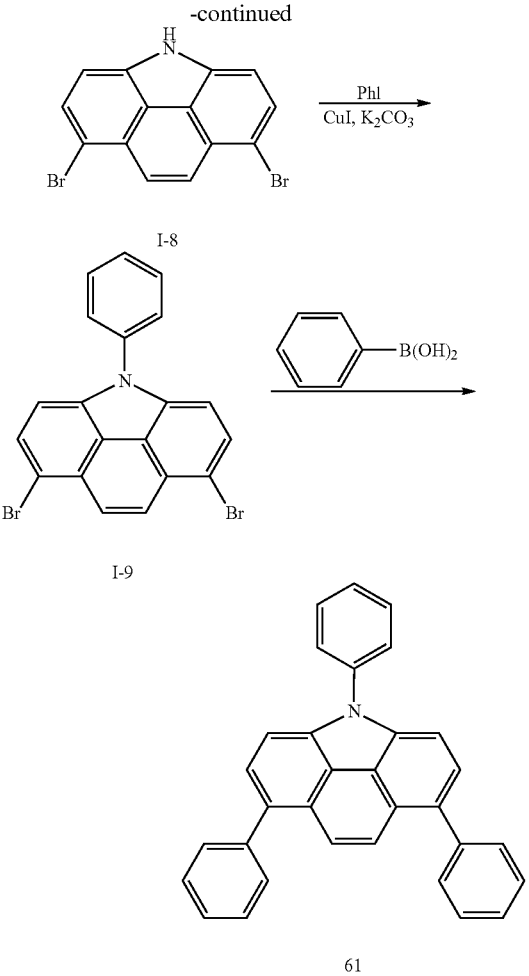

Synthesis of Intermediate I-8

1.91 g (10.0 mmol) of 6H-benzo[def]carbazole was completely dissolved in 60 mL of carbon tetrachloride ($CCl_4$), 3.56 g (20.0 mmol) of N-bromosuccinimide was added to the solution, and the mixture was agitated at 80° C. for 30 minutes. The reaction solution was cooled down to room temperature and agitated for 30 minutes, extracting a crystal. The collected crystal was washed by using a pressure-reducing filter and washed with methanol, obtaining 1.71 g of a white crystal intermediate I-1 (49% of a yield). The produced compound was examined through LC-MS. $C_{14}H_7Br_2N$: $M^+$ 346.9

Synthesis of Intermediate I-9

10.0 g (28.7 mmol) of the intermediate I-1, 7.0 g (34.4 mmol) of iodobenzene, 0.5 g (2.87 mmol) of 1,10-phenanthroline, 1.1 g (5.74 mmol) of CuI, and 11.9 g (86.1 mmol) of $K_2CO_3$ were dissolved in 100 mL of DMF (Dimethylformamide), and the solution was agitated at 80° C. for 24 hours. The reaction solution was cooled down to room temperature and extracted with 100 mL of water. The collected organic layer was dried with magnesium sulfate, and a remnant obtained by evaporating a solvent therein was separated and purified through silica gel column chromatography, obtaining 9.51 g of an intermediate I-2 (78% of a yield). The produced compound was examined through LC-MS. $C_{20}H_{11}Br_2N$: $M^+$ 422.9

Synthesis of Compound 61

1.6 g of a compound 61 was obtained according to the same method as the compound 1 was synthesized except for using the intermediate I-9 instead of the intermediate I-5 (75% of a yield). The produced compound was examined through MS/FAB and $^1H$ NMR. $C_{32}H_{21}N$ cal. 419.52. found 420.52. $^1H$ NMR (CDCl$_3$, 400 MHz) δ 8.14-8.11 (m, 4H), 8.13 (s, 1H), 8.11 (s, 1H), 8.06-7.97 (m, 8H), 7.91-7.83 (m, 5H), 7.47 (s, 2H)

Compounds in the following Table 1 were synthesized according to a similar method to Reaction Schemes 1 to 3. The examination data of the compound are provided as follows. Specifically, the intermediates in Reaction Schemes 1 to 3 (—Br or —B(OH)$_2$ were used to synthesize most of compounds in a similar synthesis method to the above method.

TABLE 1

| Compound | $^1H$ NMR (CDCl$_3$, 400 MHz) | MS/FAB found | calc. |
|---|---|---|---|
| 1 | d = 8.02 (m, 2H), 7.87-7.84 (s, 4H), 7.93-7.88 (m, 2H), 7.86 (m, 2H), 7.84-7.80 (m, 4H), 7.77-7.65 (m, 5H), 7.59 (d, 2H) | 420.17 | 419.17 |
| 3 | d = 8.21-7.92 (m, 11H), 7.74-7.37 (m, 12H), 7.22 (s, 1H), 6.84-6.82 (m, 1H), 6.50-6.39 (m, 1H), 5.99-5.95 (m, 1H), 5.45-5.33 (m, 1H), 4.83-4.71 (m, 1H) | 668.23 | 667.23 |
| 4 | d = 8.17 (m, 1H), 8.22-8.16 (m, 4H), 8.06-8.04 (m, 2H), 7.9.-7.88 (m, 6H), 7.82-7.78 (m, 2H), 7.76-7.73 (m, 3H), 7.70-7.65 (m, 3H), 7.55-7.51 (m, 2H), 7.46-7.42 (m, 2H) | 520.20 | 519.20 |
| 12 | d = 8.02 (m, 2H), 7.98-7.95 (dd, 2H), 7.90-7.88 (m, 2H), 7.82-7.78 (m, 6H), 7.66-7.55 (m, 5H), 7.45-7.44 (d, 2H), 7.41-7.26 (m, 24H), 7.04-7.02 (m, 2H) | 890.36 | 899.36 |
| 13 | d = 8.65-8.63 (m. 2H), 8.55-8.53 (m, 2H), 8.44 (m, 2H), 8.27 (m, 2H), 8.14-8.12 (m, 2H), 8.01-7.99 (m, 2H), 7.88-7.55 (m, 15H), 7.38-7.34 (m, 2H) | 620.23 | 619.23 |
| 18 | d = 8.00 (m, 2H), 7.83-7.78 (m, 6H), 7.76 (d, 2H), 7.67-7.63 (m, 2H), 7.60-7.55 (m, 5H), 7.29 (d, 2H), 1.39 (s, 18H) | 532.29 | 531.29 |
| 21 | d = 8.06 (m, 2H), 8.06-8.00 (m, 8H), 7.83-7.76 (m, 4H), 7.67-7.55 (m, 3H), 7.50-7.49 (d, 2H) | 582.29 | 581.29 |
| 23 | d = 8.57 (m, 2H), 8.36-8.34 (m, 4H), 8.26 (m, 2H), 8.21-8.18 (m, 4H), 8.04-7.96 (m, 8H), 7.83-7.76 (m, 4H), 7.66-7.56 (m, 7H), 7.50-7.49 (s, 2H), 7.34-7.30 (m, 4H) | 772.29 | 771.29 |
| 25 | d = 7.96 (m, 2H), 7.91-7.76 (m, 12H), 7.67-7.55 (m, 3H), 7.41 (d, 2H), 0.35 (s, 18H) | 564.25 | 563.25 |
| 27 | d = 8.46-8.43 (m, 1H), 8.14-7.40 (m, 29H), 7.30 (s, 2H), 6.84-6.82 (d, 1H), 6.50-6.38 (m, 1H), 5.98-5.95 (m, 1H), 3.45-3.35 (m, 2H), 2.83-2.71 (m, 2H) | 822.31 | 821.31 |
| 28 | d = 8.06 (m, 2H), 7.84-7.80 (m, 4H), 7.76-7.72 (m, 4H), 7.63-7.58 (m, 6H), 7.56 (m, 2H), 7.53-7.49 (m, 4H), 7.46-7.35 (m, 5H), 7.30-7.29 (d, 2H) | 572.13 | 571.13 |
| 34 | d = 8.16 (m, 4H), 8.01-7.85 (m, 8H), 7.82-7.69 (m, 6H), 7.56-7.55 (d, 2H), 7.47-7.44 (m, 2H), 7.38-7.33 (m, 2H) | 538.19 | 537.19 |
| 37 | d = 8.16 (m, 4H), 8.03-7.83 (m, 10H), 7.76-7.69 (m, 6H), 7.64-7.59 (m, 3H), 7.54-7.50 (m, 2H), 7.36-7.35 (d, 2H) | 570.21 | 569.21 |
| 38 | d = 8.21-7.38 (m, 25H), 7.21 (s, 1H), 6.84-6.82 (d, 1H), 6.49-6.38 (m, 1H), 5.98-5.95 (m, 1H), 5.45-5.35 (m, 2H), 4.83-4.62 (m, 2H) | 720.26 | 719.26 |
| 42 | d = 8.27 (m, 2H), 8.11-7.06 (m, 12H), 7.93-7.88 (m, 4H), 7.80-7.65 (m, 15H), 7.62-7.61 (d, 1H), 7.60 (d, 2H), 7.58 (d, 1H) | 772.29 | 771.29 |
| 46 | d = 8.17 (m, 1H), 8.02 (m, 1H), 7.92-7.84 (m, 4H), 7.76-7.74 (m, 1H), 7.63-7.35 (m, 13H), 7.29 (d, 1H), 7.25-7.13 (m, 2H) | 470.18 | 469.18 |
| 54 | d = 8.02 (m, 1H), 7.97-7.96 (m, 1H), 7.87-7.84 (m, 2H), 7.83-7.69 (m, 16H), 7.67-7.55 (m, 4H), 7.53-7.48 (m, 7H), 7.46-7.41 (m, 4H) | 678.25 | 677.25 |
| 61 | d = 8.14-8.11 (m, 4H), 8.13 (s, 1H), 8.11 (s, 1H), 8.06-7.97 (m, 8H), 7.91-7.83 (m, 5H), 7.47 (s, 2H) | 420.17 | 419.17 |
| 63 | d = 8.46-8.44 (ss, 2H), 8.64-7.49 (m, 12H), 8.37-8.33 (ss, 2H), 8.21-8.14 (m, 4H), 8.05-8.00 (m, 4H), 7.90-7.83 (m, 1H), 7.80-7.78 (ss, 2H), 7.37 (s, 2H) | 668.23 | 667.23 |
| 67 | d = 7.66 (s, 1H), 7.64 (s, 1H), 7.60-7.57 (m, 12H), 7.57-7.49 (m, 4H), 7.44-7.41 (m, 4H), 7.40-7.36 (m, 1H), 7.34 (s, 1H), 7.32-7.28 (m, 17H), 7.26-7.22 (m, 6H), 7.09 (s, 2H) | 936.34 | 935.34 |
| 72 | d = 7.90-7.85 (m, 4H), 7.69-7.67 (ss, 2H), 7.56-7.33 (m, 9H), 7.27-7.25 (ss, 2H), 7.22-7.06 (m, 24H), 7.02 (s, 2H), 6.84-6.82 (m, 2H) | 900.36 | 899.36 |
| 73 | d = 8.67-8.65 (m, 2H), 8.36-8.34 (m, 2H), 8.00 (s, 2H), 7.87-7.85 (ss, 2H), 7.76-7.54 (m, 10H), 7.46-7.43 (m, 2H), 7.34-7.29 (m, 4H), 7.14-7.10 (m, 2H), 6.77 (s, 2H), 1.33 (s, 9H) | 676.29 | 675.29 |
| 79 | d = 8.26 (m, 2H), 8.13 (m, 2H), 8.00-7.89 (m, 6H), 7.74-7.72 (m, 2H), 7.63-7.37 (m, 17H), 7.33-7.31 (ss, 2H), 7.12 (s, 2H) | 672.26 | 671.26 |
| 81 | d = 7.79-7.72 (m, 8H), 7.67-7.65 (ss, 2H), 7.56-7.48 (m, 4H), 7.40-7.36 (m, 1H), 7.34-7.31 (ss, 2H), 7.09 (s, 2H) | 582.29 | 581.29 |
| 86 | d = 8.12-8.10 (m, 4H), 7.92-7.86 (m, 6H), 7.76-7.69 (m, 4H), 7.60-7.45 (m, 19H), 7.09 (s, 2H) | 750.28 | 749.28 |
| 88 | d = 8.37-8.32 (m, 1H), 8.15-8.14 (m, 1H), 8.00-7.92 (m, 10H), 7.81-7.78 (m, 4H), 7.72-7.66 (m, 8H), 7.62-7.53 (m, 10H), 7.09 (s, 2H) | 737.29 | 736.29 |
| 92 | d = 7.81-7.79 (m, 2H), 7.77-7.71 (m, 6H), 7.67-7.61 (m, 6H), 7.56-7.48 (m, 6H), 7.40-7.28 (m, 7H), 7.16-7.09 (m, 6H), 1.36 (s, 12H) | 804.36 | 803.36 |

TABLE 1-continued

| Compound | $^1$H NMR (CDCl$_3$, 400 MHz) | MS/FAB found | MS/FAB calc. |
|---|---|---|---|
| 97 | d = 8.32-8.30 (m, 2H), 8.14-7.61 (m, 17H), 7.57-7.55 (ss, 2H), 7.49-7.45 (m, 2H), 7.18-7.14 (m, 2H), 6.98 (s, 2H) | 570.21 | 569.21 |
| 101 | d = 8.29 (s, 4H), 8.23-8.21 (ss, 4H), 8.19-8.11 (m, 6H), 8.03-8.01 (ss, 4H), 7.83-7.77 (m, 4H), 8.73-7.66 (m, 4H), 7.62-7.56 (m, 3H), 7.52-7.50 (ss, 2H), 7.43 (s, 2H) | 744.26 | 743.26 |
| 102 | d = 7.96-7.94 (m, 2H), 7.83-7.76 (m, 8H), 7.73-7.71 (ss, 2H), 7.67-7.55 (m, 12H), 7.51-7.47 (m, 13H) | 772.29 | 771.29 |
| 114 | d = 8.14-8.11 (m, 2H), 7.86-7.67 (m, 14H), 7.64-7.56 (m, 5H), 7.54-7.42 (m, 12H), 7.31-7.28 (ss, 1H), 7.18-7.16 (ss, 1H) | 678.25 | 677.25 |

(Manufacture of Organic Light Emitting Diode)

The following Examples and Comparative Examples are provided in order to highlight characteristics of one or more embodiments, but it is to be understood that the Examples and Comparative Examples are not to be construed as limiting the scope of the embodiments, nor are the Comparative Examples to be construed as being outside the scope of the embodiments. Further, it is to be understood that the embodiments are not limited to the particular details described in the Examples and Comparative Examples.

Example 1

An anode was manufactured by cutting a 15 Ω/cm$^2$ (1200 Å) ITO glass substrate (Corning Inc.) into a size of 50 mm×50 mm×0.7 mm, ultrasonic wave-washing the glass substrate with isopropyl alcohol and pure water respectively for 5 minutes, radiating an ultraviolet (UV) ray for 30 minutes, cleaning the glass substrate by exposing it to ozone, and then, mounting this glass substrate in a vacuum deposition apparatus.

On the substrate, 2-TNATA was vacuum-deposited to form a 600 Å-thick hole injection layer (HIL), and subsequently, a hole transport material, 4,4'-bis[N-(1-naphthyl)-N-phenylamino]biphenyl (Hereinafter, NPB) as a hole transporting compound was vacuum-deposited to be a 300 Å-thick hole transport layer (HTL).

On the hole transport layer (HTL), the compound 1 as a blue fluorescent host and 4,4'-bis[2-(4-(N,N-diphenylamino)phenyl)vinyl]biphenyl (hereinafter, DPAVBi) as a blue fluorescent dopant were simultaneously deposited in a weight ratio of 98:2 to form a 300 Å-thick emission layer.

Subsequently, Alq3 was deposited to form a 300 Å-thick electron transport layer (ETL) on the emission layer upper, a halogenated alkaline metal, LiF, was deposited to form a 10 Å-thick electron injection layer (EIL) on the electron transport layer (ETL), and Al was vacuum-deposited to form a 3000 Å-thick LiF/Al electrode (a cathode), manufacturing an organic light emitting diode.

Example 2

An organic light emitting diode was manufactured according to the same method as Example 1 except for using the compound 3 instead of the compound 1 to form an emission layer.

Example 3

An organic light emitting diode was manufactured according to the same method as Example 1 except for using the compound 8 instead of the compound 1 to form an emission layer.

Example 4

An organic light emitting diode was manufactured according to the same method as Example 1 except for using the compound 12 instead of the compound 1 to form an emission layer.

Example 5

An organic light emitting diode was manufactured according to the same method as Example 1 except for using the compound 21 instead of the compound 1 to form an emission layer.

Example 6

An organic light emitting diode was manufactured according to the same method as Example 1 except for using the compound 37 instead of the compound 1 to form an emission layer.

Example 7

An organic light emitting diode was manufactured according to the same method as Example 1 except for using the compound 42 instead of the compound 1 to form an emission layer.

Example 8

An organic light emitting diode was manufactured according to the same method as Example 1 except for using the compound 54 instead of the compound 1 to form an emission layer.

Comparative Example 1

An organic light emitting diode was manufactured according to the same method as Example 1 except for using 9,10-di-naphthalene-2-yl-anthracene (hereinafter, DNA) as a blue fluorescent host instead of the compound 1 to form an emission layer.

(Performance Measurement of Organic Light Emitting Diode)

Current density, luminance changes, efficiency, and lifespan depending on voltage and luminous efficiency of each organic light emitting diode according to Examples 1 to 8 and Comparative Example 1 were measured. The measurements were specifically performed by the following methods. The results are shown in the following Table 1.

1) Measurement of Current Density Change Depending on Voltage Change

The manufactured organic light emitting diodes were measured for current value flowing in the unit device, while increasing the voltage using a current-voltage meter (Keithley 2400), and the measured current value was divided by an area to provide the result.

2) Measurement of Luminance Change Depending on Voltage Change

The organic light emitting diodes were measured for luminance, while increasing the voltage using a luminance meter (Minolta Cs-1000A).

3) Measurement of Luminous Efficiency and Electric Power Efficiency

Luminous efficiency and electric power efficiency were calculated by using the luminance, current density, and voltage (V) that are measured in "1) Measurement of Current density Change depending on Voltage change" and "2) Measurement of Luminance Change depending on Voltage change", and the results are shown in Table 1.

4) Measurement of Life-Span

Luminance change of the organic light emitting diodes was measured by constantly inputting a current corresponding to reference luminance.

TABLE 2

| | Light emitting material | Driving voltage (V) | Current density (mA/cm$^2$) | Luminance (cd/m$^2$) | Efficiency (cd/A) | Light emitting color | Half-life life-span (hr@100 mA/cm$^2$) |
|---|---|---|---|---|---|---|---|
| Example 1 | compound 1 | 6.01 | 50 | 2,940 | 5.88 | blue | 302 hr |
| Example 2 | compound 3 | 6.18 | 50 | 2,960 | 5.92 | blue | 276 hr |
| Example 3 | compound 8 | 6.09 | 50 | 3,105 | 6.21 | blue | 322 hr |
| Example 4 | compound 12 | 6.05 | 50 | 3,035 | 6.07 | blue | 317 hr |
| Example 5 | compound 21 | 6.16 | 50 | 3,090 | 6.18 | blue | 337 hr |
| Example 6 | compound 37 | 6.13 | 50 | 3,030 | 6.06 | blue | 319 hr |
| Example 7 | compound 42 | 6.24 | 50 | 3,220 | 6.44 | blue | 293 hr |
| Example 7 | compound 54 | 6.29 | 50 | 2,980 | 5.96 | blue | 293 hr |
| Comparative Example 1 | DNA | 7.35 | 50 | 2,065 | 4.13 | blue | 145 hr |

In the above Table 2, it can be seen that when compounds according to exemplary embodiments were used as a host material of a blue emission layer, a driving voltage and efficiency were improved. Specifically, the life-span was remarkably improved compared with a conventional material, DNA (9,10-di-naphthalene-2-yl-anthracene).

By way of summation and review, examples of an organic optoelectronic device include an organic photoelectric device, an organic light emitting diode, an organic solar cell, an organic photo conductor drum, an organic transistor, and the like, which include a hole injecting or transport material, an electron injecting or transport material, or a light emitting material.

An organic light emitting diode (OLED) has recently drawn attention due to an increase in demand for flat panel displays. In general, an organic light emitting diode converts electrical energy into photo-energy (e.g., light) by applying current to an organic light emitting material. An organic light emitting diode may have a structure in which a functional organic material layer is interposed between an anode and a cathode. The organic material layer may include a multilayer including different materials, for example a hole injection layer (HIL), a hole transport layer (HTL), an emission layer, an electron transport layer (ETL), or an electron injection layer (EIL), in order to improve efficiency and stability of an organic photoelectric device.

In such an organic light emitting diode, when a voltage is applied between an anode and a cathode, holes from the anode and electrons from the cathode are injected to an organic material layer and combine to generate excitons having high energy. The generated excitons generate light having certain wavelengths while shifting to a ground state.

Recently, phosphorescent light emitting materials have be used as a light emitting material of an organic light emitting diode in addition to a fluorescent light emitting material. Such a phosphorescent material emits lights by a process that includes transporting electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, or the like. The light emitting material may be classified as blue, green, and red light emitting materials according to emitted colors, and yellow and orange light emitting materials to emit colors approaching natural colors.

When a single material is used as a light emitting material, a maximum light emitting wavelength may be shifted to a long wavelength or color purity may decrease because of interactions between molecules. Device efficiency may decrease because of a light emitting quenching effect. Therefore, a host/dopant system may be included as a light emitting material in order to improve color purity and increase luminous efficiency and stability through energy transfer.

In order to implement excellent performance of an organic light emitting diode, it is desirable that a material constituting an organic material layer, for example a hole injection material, a hole transport material, a light emitting material, an electron transport material, an electron injection material, and a light emitting material such as a host and/or a dopant, be stable and have good efficiency. It is desirable that the development of organic material layer forming material for an organic light emitting diode or other organic optoelectronic devices be improved.

The low molecular organic light emitting diode is manufactured as a thin film in a vacuum deposition method and may have good efficiency and life-span performance. A polymer organic light emitting diode may be manufactured in an inkjet or spin coating method has an advantage of low initial cost and being large-sized.

Both low molecular organic light emitting diodes and polymer organic light emitting diodes may have an advantage of self-light emitting, high speed response, wide viewing angle, ultra-thin, high image quality, durability, large driving temperature range, or the like. In particular, these materials may have good visibility due to self-light emitting characteristics compared with a conventional LCD (liquid crystal display) and may have an advantage of decreasing thickness and weight of LCD up to a third, because they do not need a backlight.

In addition, such materials have a response speed 1,000 times faster in microsecond units than LCDs, Accordingly, a perfect motion picture without an after-image may be provided. Based on these advantages, low molecular organic light emitting diodes and polymer organic light emitting diodes have been remarkably developed to have 80 times the efficiency and more than 100 times the life-span since such materials were first developed in the late 1980s.

Recently, larger display panels, such as a 40-inch organic light emitting diode panel, have been developed. It is desirable to have improved luminous efficiency and life-span in such panels. Accordingly, the development of stable and efficient organic material layer materials for an organic light emitting diode continues to be desirable.

Embodiments provide a compound that is capable of providing an organic optoelectronic device having characteristics such as high efficiency, long life-span, and the like. Embodiments also provide an organic light emitting diode including the compound and a display device including the organic light emitting diode.

An organic optoelectronic device including the compound according to embodiments has excellent electrochemical and thermal stability, and life-span characteristics, and high luminous efficiency at a driving voltage. In addition, the compound may be appropriate for a solution process.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:

1. A compound for an organic optoelectronic device, the compound being represented by the following Chemical Formula 1:

[Chemical Formula 1]

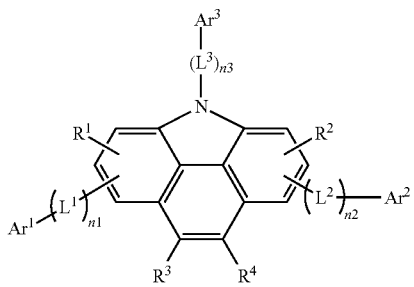

wherein, in the above Chemical Formula 1,
$Ar^1$ and $Ar^2$ are each independently a substituted or unsubstituted C6 to C30 aryl group, or a substituted or unsubstituted C2 to C30 heteroaryl group,
$R^1$ to $R^4$ and $Ar^3$ are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group,
$L^1$ to $L^3$ are each independently a substituted or unsubstituted C6 to C30 arylene group or a substituted or unsubstituted C2 to C30 heteroarylene group, and
n1 to n3 are each independently integers of 0 to 3.

2. The compound for an organic optoelectronic device as claimed in claim 1, wherein the compound for an organic optoelectronic device is represented by the following Chemical Formula 2:

[Chemical Formula 2]

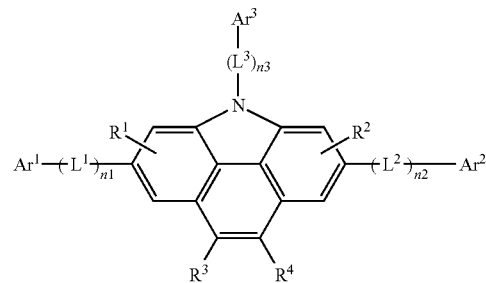

wherein in the above Chemical Formula 2,
$Ar^1$ and $Ar^2$ are each independently a substituted or unsubstituted C6 to C30 aryl group, or a substituted or unsubstituted C2 to C30 heteroaryl group,
$R^1$ to $R^4$ and $Ar^3$ are each independently hydrogen, deuterium, a substituted or unsubstituted C1 to C30 alkyl group, a substituted or unsubstituted C3 to C30 cycloalkyl group, a substituted or unsubstituted C6 to C30 aryl group, a substituted or unsubstituted C2 to C30 heteroaryl group, or a substituted or unsubstituted silyl group,
$L^1$ to $L^3$ are each independently a substituted or unsubstituted C6 to C30 arylene group or a substituted or unsubstituted C2 to C30 heteroarylene group, and
n1 to n3 are each independently integers of 0 to 3.

3. The compound for an organic optoelectronic device as claimed in claim 1, wherein $Ar^1$ and $Ar^2$ are each independently a substituted or unsubstituted C6 to C30 aryl group.

4. The compound for an organic optoelectronic device as claimed in claim 1, wherein $Ar^1$ and $Ar^2$ are each independently a substituted or unsubstituted phenyl group, a substituted or unsubstituted biphenyl group, a substituted or unsubstituted naphthyl group, a substituted or unsubstituted anthracenyl group, or a substituted or unsubstituted phenanthrenyl group.

5. The compound for an organic optoelectronic device as claimed in claim 1, wherein at least one of $Ar^1$ and $Ar^2$ is a substituted or unsubstituted dibenzofuranyl group, a substituted or unsubstituted dibenzothiophenyl group, a substituted or unsubstituted carbazolyl group, or a substituted or unsubstituted fluorenyl group.

6. The compound for an organic optoelectronic device as claimed in claim 1, wherein $L^1$ to $L^3$ are each independently a substituted or unsubstituted phenylene group, or a substituted or unsubstituted naphthalene group.

7. The compound for an organic optoelectronic device as claimed in claim 1, wherein $Ar^3$ is a substituted or unsubstituted phenyl group, or a substituted or unsubstituted biphenyl group.

8. The compound for an organic optoelectronic device as claimed in claim 1, wherein at least one of $Ar^1$ and $Ar^2$ is a C6 to C30 aryl group substituted with a C1 to 10 alkyl group, a silyl group, a cyano group, deuterium, or a halogen.

9. An organic light emitting diode, comprising
   an anode,
   a cathode, and
   at least one organic thin layer interposed between the anode and cathode,
   wherein at least one organic thin layer includes the compound according to claim 1.

10. The organic light emitting diode as claimed in claim 9, wherein the organic thin layer includes an electron injection layer (EIL), an electron transport layer (ETL), a hole injection layer (HIL), a hole transport layer (HTL), or an emission layer.

11. The organic light emitting diode as claimed in claim 9, wherein the organic thin layer is an electron injection layer (EIL), or an electron transport layer (ETL).

12. The organic light emitting diode as claimed in claim 9, wherein the organic thin layer is an emission layer.

13. The organic light emitting diode as claimed in claim 9, wherein the compound is a host in an emission layer.

14. The organic light emitting diode as claimed in claim 9, wherein the compound is a red, green, blue, or white host in an emission layer.

15. A display device comprising the organic light emitting diode as claimed in claim 9.

\* \* \* \* \*